US008574235B2

(12) United States Patent
Stone

(10) Patent No.: US 8,574,235 B2
(45) Date of Patent: Nov. 5, 2013

(54) METHOD FOR TROCHANTERIC REATTACHMENT

(75) Inventor: Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 116 days.

(21) Appl. No.: 13/111,564

(22) Filed: May 19, 2011

(65) Prior Publication Data

US 2011/0224799 A1 Sep. 15, 2011

Related U.S. Application Data

(63) Continuation-in-part of application No. 12/938,902, filed on Nov. 3, 2010, which is a continuation-in-part of application No. 12/915,962, filed on Oct. 29, 2010, which is a continuation-in-part of application No. 12/719,337, filed on Mar. 8, 2010, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 13/111,564, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, which is a continuation-in-part of application No. 11/347,661, filed on Feb. 3, 2006, now Pat. No. 7,749,250, application No. 13/111,564, which is a continuation-in-part of application No. 12/702,067, filed on Feb. 8, 2010, which is a continuation of application No. 11/541,505, filed on Sep. 29, 2006, now Pat. No. 7,658,751, application No. 13/111,564, which is a continuation-in-part of application No. 12/196,398, filed on Aug. 22, 2008, now Pat. No. 7,959,650, which is a continuation-in-part of application No. 11/784,821, filed on Apr. 10, 2007.

(51) Int. Cl.
*A61B 17/82* (2006.01)

(52) U.S. Cl.
USPC .................. 606/74; 623/22.11; 623/19.11

(58) Field of Classification Search
CPC .................. A61B 17/82; A61F 2/28
USPC .............. 606/69–75; 623/19.11–19.14, 22.11
See application file for complete search history.

(56) References Cited

U.S. PATENT DOCUMENTS

| | | |
|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |

| | | | | | |
|---|---|---|---|---|---|
| 2,329,398 A | 9/1943 | Duffy | 3,867,944 A | 2/1975 | Samuels |
| RE22,857 E | 3/1947 | Ogburn | 3,871,368 A | 3/1975 | Johnson et al. |
| 2,526,959 A | 10/1950 | Lorenzo | 3,871,379 A | 3/1975 | Clarke |
| 2,528,456 A | 10/1950 | Stevenson | 3,874,388 A | 4/1975 | King et al. |
| 2,562,419 A | 7/1951 | Ferris | 3,875,648 A | 4/1975 | Bone |
| 2,581,564 A | 1/1952 | Villegas | 3,877,570 A | 4/1975 | Barry |
| 2,600,395 A | 6/1952 | Domoj et al. | 3,880,156 A | 4/1975 | Hoff |
| 2,610,631 A | 9/1952 | Calicchio | 3,881,475 A | 5/1975 | Gordon et al. |
| 2,665,597 A | 1/1954 | Hill | 3,889,666 A | 6/1975 | Lerner |
| 2,669,774 A | 2/1954 | Mitchell | 3,892,240 A | 7/1975 | Park |
| 2,698,986 A | 1/1955 | Brown | 3,896,500 A | 7/1975 | Rambert et al. |
| 2,760,488 A | 8/1956 | Pierce | 3,907,442 A | 9/1975 | Reid |
| 2,833,284 A | 5/1958 | Springer | 3,910,281 A | 10/1975 | Kletschka et al. |
| 2,846,712 A | 8/1958 | Markman | 3,918,444 A | 11/1975 | Hoff et al. |
| 2,860,393 A | 11/1958 | Brock | 3,918,455 A | 11/1975 | Coplan |
| 2,880,728 A | 4/1959 | Rights | 3,927,666 A | 12/1975 | Hoff |
| 2,881,762 A | 4/1959 | Lowrie | 3,931,667 A | 1/1976 | Merser et al. |
| 2,883,096 A | 4/1959 | Dawson | 3,933,153 A | 1/1976 | Csatary et al. |
| 2,913,042 A | 11/1959 | Taylor | 3,937,217 A | 2/1976 | Kosonen et al. |
| 3,000,009 A | 9/1961 | Selstad | 3,943,932 A | 3/1976 | Woo |
| 3,003,155 A | 10/1961 | Mielzynski et al. | 3,946,446 A | 3/1976 | Schofield |
| 3,013,559 A | 12/1961 | Thomas | 3,946,728 A | 3/1976 | Bettex et al. |
| 3,037,619 A | 6/1962 | Stevans | 3,946,740 A | 3/1976 | Bassett |
| 3,039,460 A | 6/1962 | Chandler | 3,953,896 A | 5/1976 | Treace |
| 3,090,386 A | 5/1963 | Curtis | 3,954,103 A | 5/1976 | Garcia-Roel et al. |
| 3,103,666 A | 9/1963 | Bone | 3,961,632 A | 6/1976 | Moossun |
| 3,123,077 A | 3/1964 | Alcamo | 3,973,560 A | 8/1976 | Emmett et al. |
| 3,125,095 A | 3/1964 | Kaufman et al. | 3,976,079 A | 8/1976 | Samuels et al. |
| 3,209,422 A | 10/1965 | Dritz | 3,977,050 A | 8/1976 | Perez et al. |
| 3,234,938 A | 2/1966 | Robinson | 3,979,799 A | 9/1976 | Merser et al. |
| 3,240,379 A | 3/1966 | Bremer et al. | 3,985,138 A | 10/1976 | Jarvik |
| 3,250,271 A | 5/1966 | Lippes | 3,990,619 A | 11/1976 | Russell |
| 3,399,432 A | 9/1968 | Merser | 4,005,707 A | 2/1977 | Moulding, Jr. |
| 3,409,014 A | 11/1968 | Shannon | 4,006,747 A | 2/1977 | Kronenthal et al. |
| RE26,501 E | 12/1968 | Kendrick et al. | 4,007,743 A | 2/1977 | Blake |
| 3,435,475 A | 4/1969 | Bisk | 4,013,071 A | 3/1977 | Rosenberg et al. |
| 3,467,089 A | 9/1969 | Hasson | 4,026,281 A | 5/1977 | Mayberry et al. |
| 3,470,834 A | 10/1969 | Bone | 4,036,101 A | 7/1977 | Burnett |
| 3,470,875 A | 10/1969 | Johnson | 4,050,100 A | 9/1977 | Barry |
| 3,500,820 A | 3/1970 | Almen | 4,054,954 A | 10/1977 | Nakayama et al. |
| 3,507,274 A | 4/1970 | Soichet | 4,085,466 A | 4/1978 | Goodfellow et al. |
| 3,513,484 A | 5/1970 | Hausner | 4,094,313 A | 6/1978 | Komamura et al. |
| 3,515,132 A | 6/1970 | McKnight | 4,099,750 A | 7/1978 | McGrew |
| 3,522,803 A | 8/1970 | Majzlin | 4,103,690 A | 8/1978 | Harris |
| 3,527,223 A | 9/1970 | Shein | RE29,819 E | 10/1978 | Bone |
| 3,533,406 A | 10/1970 | Hutterer et al. | 4,121,487 A | 10/1978 | Bone |
| 3,541,591 A | 11/1970 | Hoegerman | 4,143,656 A | 3/1979 | Holmes et al. |
| 3,547,389 A | 12/1970 | Mitchell | 4,144,876 A | 3/1979 | DeLeo |
| 3,579,831 A | 5/1971 | Stevens et al. | 4,149,277 A | 4/1979 | Bokros |
| 3,590,616 A | 7/1971 | Schussler | 4,157,714 A | 6/1979 | Foltz et al. |
| 3,608,095 A | 9/1971 | Barry | 4,160,453 A | 7/1979 | Miller |
| 3,618,447 A | 11/1971 | Goins | 4,164,225 A | 8/1979 | Johnson et al. |
| 3,628,530 A | 12/1971 | Schwartz | 4,172,458 A | 10/1979 | Pereyra |
| 3,643,649 A | 2/1972 | Amato | 4,175,555 A | 11/1979 | Herbert et al. |
| 3,648,705 A | 3/1972 | Lary | 4,185,636 A | 1/1980 | Gabbay et al. |
| 3,656,483 A | 4/1972 | Rudel | 4,196,883 A | 4/1980 | Einhorn et al. |
| 3,659,597 A | 5/1972 | Wolfers | 4,210,148 A | 7/1980 | Stivala |
| 3,664,345 A | 5/1972 | Dabbs et al. | 4,235,161 A | 11/1980 | Kunreuther |
| 3,665,560 A | 5/1972 | Bennett et al. | 4,235,238 A | 11/1980 | Ogiu et al. |
| 3,675,639 A | 7/1972 | Cimber | 4,237,779 A | 12/1980 | Kunreuther |
| 3,683,422 A | 8/1972 | Stemmer et al. | 4,243,037 A | 1/1981 | Smith |
| 3,692,022 A | 9/1972 | Ewing | 4,249,525 A | 2/1981 | Krzeminski |
| 3,695,271 A | 10/1972 | Chodorow | 4,263,913 A | 4/1981 | Malmin |
| 3,699,969 A | 10/1972 | Allen | 4,265,246 A | 5/1981 | Barry |
| 3,716,058 A | 2/1973 | Tanner, Jr. | 4,273,117 A | 6/1981 | Neuhauser et al. |
| 3,744,488 A | 7/1973 | Cox | 4,275,717 A | 6/1981 | Bolesky |
| 3,752,516 A | 8/1973 | Mumma | 4,287,807 A | 9/1981 | Pacharis et al. |
| 3,757,629 A | 9/1973 | Schneider | 4,291,698 A | 9/1981 | Fuchs et al. |
| 3,763,856 A | 10/1973 | Blomberg | 4,301,551 A | 11/1981 | Dore et al. |
| 3,771,520 A | 11/1973 | Lerner | 4,307,723 A | 12/1981 | Finney |
| 3,777,748 A | 12/1973 | Abramson | 4,312,337 A | 1/1982 | Donohue |
| 3,807,407 A | 4/1974 | Schweizer | 4,316,469 A | 2/1982 | Kapitanov et al. |
| 3,810,456 A | 5/1974 | Karman | 4,326,531 A | 4/1982 | Shimonaka et al. |
| 3,825,010 A | 7/1974 | McDonald | 4,345,601 A | 8/1982 | Fukuda |
| 3,840,017 A | 10/1974 | Violante et al. | 4,349,027 A | 9/1982 | DiFrancesco |
| 3,842,824 A | 10/1974 | Neufeld | 4,388,921 A | 6/1983 | Sutter et al. |
| 3,842,840 A | 10/1974 | Schweizer | 4,400,833 A | 8/1983 | Kurland |
| 3,845,772 A | 11/1974 | Smith | 4,402,445 A | 9/1983 | Green |
| 3,867,933 A | 2/1975 | Kitrilakis | 4,409,974 A | 10/1983 | Freedland |

| | | |
|---|---|---|
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |

| | | | | | | |
|---|---|---|---|---|---|---|
| 5,100,415 | A | 3/1992 | Hayhurst | 5,320,626 | A | 6/1994 | Schmieding |
| 5,100,417 | A | 3/1992 | Cerier et al. | 5,320,633 | A | 6/1994 | Allen et al. |
| 5,108,433 | A | 4/1992 | May et al. | 5,324,308 | A | 6/1994 | Pierce |
| 5,116,337 | A | 5/1992 | Johnson | 5,330,489 | A | 7/1994 | Green et al. |
| 5,116,373 | A | 5/1992 | Jakob et al. | 5,333,625 | A | 8/1994 | Klein |
| 5,116,375 | A | 5/1992 | Hofmann | 5,334,204 | A | 8/1994 | Clewett et al. |
| 5,123,913 | A | 6/1992 | Wilk et al. | 5,336,229 | A | 8/1994 | Noda |
| 5,123,914 | A | 6/1992 | Cope | 5,336,231 | A | 8/1994 | Adair |
| 5,127,785 | A | 7/1992 | Faucher et al. | 5,336,240 | A | 8/1994 | Metzler et al. |
| 5,129,901 | A | 7/1992 | Decoste | 5,339,870 | A | 8/1994 | Green et al. |
| 5,129,902 | A | 7/1992 | Goble et al. | 5,342,369 | A | 8/1994 | Harryman, II |
| 5,129,904 | A | 7/1992 | Illi et al. | 5,346,462 | A | 9/1994 | Barber |
| 5,129,906 | A | 7/1992 | Ross et al. | 5,350,380 | A | 9/1994 | Goble et al. |
| 5,139,498 | A | 8/1992 | Astudillo Ley | RE34,762 | E | 10/1994 | Goble et al. |
| 5,139,499 | A | 8/1992 | Small et al. | 5,354,298 | A | 10/1994 | Lee et al. |
| 5,139,520 | A | 8/1992 | Rosenberg | 5,356,412 | A | 10/1994 | Golds et al. |
| 5,143,498 | A | 9/1992 | Whitman | 5,356,413 | A | 10/1994 | Martins et al. |
| 5,147,362 | A | 9/1992 | Goble | 5,356,417 | A | 10/1994 | Golds |
| 5,149,329 | A | 9/1992 | Richardson | 5,358,511 | A | 10/1994 | Gatturna et al. |
| 5,151,104 | A | 9/1992 | Kenna | 5,360,431 | A | 11/1994 | Puno et al. |
| 5,152,790 | A | 10/1992 | Rosenberg et al. | 5,362,294 | A | 11/1994 | Seitzinger |
| 5,154,189 | A | 10/1992 | Oberlander | 5,364,400 | A | 11/1994 | Rego, Jr. et al. |
| 5,156,616 | A | 10/1992 | Meadows et al. | 5,366,461 | A | 11/1994 | Blasnik |
| 5,163,960 | A | 11/1992 | Bonutti | 5,368,599 | A | 11/1994 | Hirsch et al. |
| D331,626 | S | 12/1992 | Hayhurst et al. | 5,370,661 | A | 12/1994 | Branch |
| 5,169,400 | A | 12/1992 | Muhling et al. | 5,370,662 | A | 12/1994 | Stone et al. |
| 5,176,682 | A | 1/1993 | Chow | 5,372,146 | A | 12/1994 | Branch |
| 5,178,629 | A | 1/1993 | Kammerer | 5,372,604 | A | 12/1994 | Trott |
| 5,183,458 | A | 2/1993 | Marx | 5,372,821 | A | 12/1994 | Badylak et al. |
| 5,192,282 | A | 3/1993 | Draenert et al. | 5,374,268 | A | 12/1994 | Sander |
| 5,197,987 | A | 3/1993 | Koch et al. | 5,374,269 | A | 12/1994 | Rosenberg |
| 5,203,784 | A | 4/1993 | Ross et al. | 5,379,492 | A | 1/1995 | Glesser |
| 5,203,787 | A | 4/1993 | Noblitt et al. | 5,383,878 | A | 1/1995 | Roger et al. |
| 5,207,679 | A | 5/1993 | Li | 5,383,904 | A | 1/1995 | Totakura et al. |
| 5,209,753 | A | 5/1993 | Biedermann et al. | 5,385,567 | A | 1/1995 | Goble |
| 5,209,805 | A | 5/1993 | Spraggins | 5,391,171 | A | 2/1995 | Schmieding |
| 5,211,647 | A | 5/1993 | Schmieding | 5,391,176 | A | 2/1995 | de la Torre |
| 5,211,650 | A | 5/1993 | Noda | 5,391,182 | A | 2/1995 | Chin |
| 5,214,987 | A | 6/1993 | Fenton, Sr. | 5,393,302 | A | 2/1995 | Clark et al. |
| 5,219,359 | A | 6/1993 | McQuilkin et al. | RE34,871 | E | 3/1995 | McGuire et al. |
| 5,222,976 | A | 6/1993 | Yoon | 5,397,356 | A | 3/1995 | Goble et al. |
| 5,224,946 | A | 7/1993 | Hayhurst et al. | 5,403,328 | A | 4/1995 | Shallman |
| 5,230,699 | A | 7/1993 | Grasinger | 5,403,329 | A | 4/1995 | Hinchcliffe |
| 5,232,436 | A | 8/1993 | Janevski | 5,403,348 | A | 4/1995 | Bonutti |
| 5,234,435 | A | 8/1993 | Seagrave, Jr. | 5,405,359 | A | 4/1995 | Pierce |
| 5,235,238 | A | 8/1993 | Nomura et al. | 5,417,691 | A | 5/1995 | Hayhurst |
| 5,236,445 | A | 8/1993 | Hayhurst et al. | 5,417,698 | A | 5/1995 | Green et al. |
| 5,236,461 | A | 8/1993 | Forte | 5,417,712 | A | 5/1995 | Whittaker et al. |
| 5,242,447 | A | 9/1993 | Borzone | 5,423,819 | A | 6/1995 | Small et al. |
| 5,246,441 | A | 9/1993 | Ross et al. | 5,423,821 | A | 6/1995 | Pasque |
| 5,249,899 | A | 10/1993 | Wilson | 5,423,823 | A | 6/1995 | Schmieding |
| 5,250,053 | A | 10/1993 | Snyder | 5,423,860 | A | 6/1995 | Lizardi et al. |
| 5,258,015 | A | 11/1993 | Li et al. | 5,425,733 | A | 6/1995 | Schmieding |
| 5,258,016 | A | 11/1993 | DiPoto et al. | 5,425,766 | A | 6/1995 | Bowald et al. |
| 5,258,040 | A | 11/1993 | Bruchman et al. | 5,433,751 | A | 7/1995 | Christel et al. |
| 5,261,908 | A | 11/1993 | Campbell, Jr. | 5,437,680 | A | 8/1995 | Yoon |
| 5,268,001 | A | 12/1993 | Nicholson et al. | 5,437,685 | A | 8/1995 | Blasnik |
| 5,269,160 | A | 12/1993 | Wood | 5,439,684 | A | 8/1995 | Prewett et al. |
| 5,269,783 | A | 12/1993 | Sander | 5,441,508 | A | 8/1995 | Gazielly et al. |
| 5,269,806 | A | 12/1993 | Sardelis et al. | 5,443,468 | A | 8/1995 | Johnson |
| 5,269,809 | A | 12/1993 | Hayhurst et al. | 5,443,482 | A | 8/1995 | Stone et al. |
| 5,279,311 | A | 1/1994 | Snyder | 5,443,483 | A | 8/1995 | Kirsch et al. |
| 5,281,422 | A | 1/1994 | Badylak et al. | 5,443,509 | A | 8/1995 | Boucher et al. |
| 5,282,809 | A | 2/1994 | Kammerer et al. | 5,445,833 | A | 8/1995 | Badylak et al. |
| 5,282,832 | A | 2/1994 | Toso et al. | 5,447,512 | A | 9/1995 | Wilson et al. |
| 5,282,867 | A | 2/1994 | Mikhail | 5,449,361 | A | 9/1995 | Preissman |
| 5,285,040 | A | 2/1994 | Brandberg et al. | 5,451,203 | A | 9/1995 | Lamb |
| 5,290,217 | A | 3/1994 | Campos | 5,454,811 | A | 10/1995 | Huebner |
| 5,290,243 | A | 3/1994 | Chodorow et al. | 5,454,821 | A | 10/1995 | Harm et al. |
| 5,306,301 | A | 4/1994 | Graf et al. | 5,456,685 | A | 10/1995 | Huebner |
| 5,312,410 | A | 5/1994 | Miller et al. | 5,456,722 | A | 10/1995 | McLeod et al. |
| 5,312,422 | A | 5/1994 | Trott | 5,458,601 | A | 10/1995 | Young, Jr. et al. |
| 5,312,438 | A | 5/1994 | Johnson | 5,458,604 | A | 10/1995 | Schmieding |
| 5,314,429 | A | 5/1994 | Goble | 5,462,542 | A | 10/1995 | Alesi, Jr. |
| 5,318,566 | A | 6/1994 | Miller | 5,462,560 | A | 10/1995 | Stevens |
| 5,318,575 | A | 6/1994 | Chesterfield et al. | 5,464,426 | A | 11/1995 | Bonutti |
| 5,318,577 | A | 6/1994 | Li | 5,464,427 | A | 11/1995 | Curtis et al. |
| 5,318,578 | A | 6/1994 | Hasson | 5,464,440 | A | 11/1995 | Johansson et al. |
| 5,320,115 | A | 6/1994 | Kenna | 5,466,237 | A | 11/1995 | Byrd, III et al. |

| Patent | Date | Inventor |
|---|---|---|
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Brånemark et al. |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |

| | | | | | | |
|---|---|---|---|---|---|---|
| 5,735,875 A | 4/1998 | Bonutti et al. | | 5,938,668 A | 8/1999 | Scirica et al. |
| 5,741,259 A | 4/1998 | Chan | | 5,941,439 A | 8/1999 | Kammerer et al. |
| 5,741,260 A | 4/1998 | Songer et al. | | 5,941,900 A | 8/1999 | Bonutti |
| 5,741,281 A | 4/1998 | Martin et al. | | 5,944,739 A | 8/1999 | Zlock et al. |
| 5,743,912 A | 4/1998 | Lahille et al. | | 5,946,783 A | 9/1999 | Plociennik et al. |
| 5,746,751 A | 5/1998 | Sherts | | 5,947,915 A | 9/1999 | Thibodo, Jr. |
| 5,746,752 A | 5/1998 | Burkhart | | 5,947,982 A | 9/1999 | Duran |
| 5,746,754 A | 5/1998 | Chan | | 5,947,999 A | 9/1999 | Groiso |
| 5,749,898 A | 5/1998 | Schulze et al. | | 5,948,002 A | 9/1999 | Bonutti |
| 5,755,729 A | 5/1998 | de la Torre et al. | | 5,951,559 A | 9/1999 | Burkhart |
| 5,755,791 A | 5/1998 | Whitson et al. | | 5,951,560 A | 9/1999 | Simon et al. |
| 5,766,176 A | 6/1998 | Duncan | | 5,954,747 A | 9/1999 | Clark |
| 5,766,218 A | 6/1998 | Arnott | | 5,957,953 A | 9/1999 | DiPoto et al. |
| 5,766,250 A | 6/1998 | Chervitz et al. | | 5,961,520 A | 10/1999 | Beck, Jr. et al. |
| 5,769,894 A | 6/1998 | Ferragamo | | 5,961,521 A | 10/1999 | Roger et al. |
| 5,769,899 A | 6/1998 | Schwartz et al. | | 5,961,524 A | 10/1999 | Crombie |
| 5,772,673 A | 6/1998 | Cuny et al. | | 5,964,764 A | 10/1999 | West, Jr. et al. |
| 5,776,196 A | 7/1998 | Matsuzaki et al. | | 5,964,767 A | 10/1999 | Tapia et al. |
| 5,782,845 A | 7/1998 | Shewchuk | | 5,964,769 A | 10/1999 | Wagner et al. |
| 5,782,862 A | 7/1998 | Bonutti | | 5,964,783 A | 10/1999 | Grafton et al. |
| 5,782,864 A | 7/1998 | Lizardi | | 5,968,045 A | 10/1999 | Frazier |
| 5,782,866 A | 7/1998 | Wenstrom, Jr. | | 5,968,047 A | 10/1999 | Reed |
| 5,785,714 A | 7/1998 | Morgan et al. | | 5,968,077 A | 10/1999 | Wojciechowicz et al. |
| 5,792,142 A | 8/1998 | Galitzer | | 5,970,697 A | 10/1999 | Jacobs et al. |
| 5,792,149 A | 8/1998 | Sherts et al. | | 5,972,006 A | 10/1999 | Sciaino, Jr. |
| 5,796,127 A | 8/1998 | Hayafuji et al. | | 5,976,125 A | 11/1999 | Graham |
| 5,797,913 A | 8/1998 | Dambreville et al. | | 5,976,127 A | 11/1999 | Lax |
| 5,797,915 A | 8/1998 | Pierson, III et al. | | 5,980,473 A | 11/1999 | Korakianitis et al. |
| 5,797,916 A * | 8/1998 | McDowell ................ 606/74 | | 5,980,524 A | 11/1999 | Justin et al. |
| 5,797,928 A | 8/1998 | Kogasaka | | 5,980,539 A | 11/1999 | Kontos |
| 5,800,407 A | 9/1998 | Eldor et al. | | 5,980,558 A | 11/1999 | Wiley |
| 5,810,824 A | 9/1998 | Chan | | 5,980,559 A | 11/1999 | Bonutti |
| 5,810,848 A | 9/1998 | Hayhurst | | 5,989,252 A | 11/1999 | Fumex |
| 5,814,056 A | 9/1998 | Prosst et al. | | 5,989,256 A | 11/1999 | Kuslich et al. |
| 5,814,069 A | 9/1998 | Schulze et al. | | 5,989,282 A | 11/1999 | Bonutti |
| 5,814,070 A | 9/1998 | Borzone et al. | | 5,993,452 A | 11/1999 | Vandewalle |
| 5,814,072 A | 9/1998 | Bonutti | | 5,993,476 A | 11/1999 | Groiso |
| 5,814,073 A | 9/1998 | Bonutti | | 5,997,542 A | 12/1999 | Burke |
| 5,823,980 A | 10/1998 | Kopfer | | 5,997,552 A | 12/1999 | Person et al. |
| 5,824,011 A | 10/1998 | Stone et al. | | 5,997,575 A | 12/1999 | Whitson et al. |
| 5,824,066 A | 10/1998 | Gross | | 6,001,100 A | 12/1999 | Sherman et al. |
| 5,830,234 A | 11/1998 | Wojciechowicz et al. | | 6,001,106 A | 12/1999 | Ryan et al. |
| 5,843,084 A | 12/1998 | Hart et al. | | 6,007,538 A | 12/1999 | Levin |
| 5,845,645 A | 12/1998 | Bonutti | | 6,007,567 A | 12/1999 | Bonutti |
| 5,846,254 A | 12/1998 | Schulze et al. | | 6,010,525 A | 1/2000 | Bonutti et al. |
| 5,848,983 A | 12/1998 | Basaj et al. | | 6,016,727 A | 1/2000 | Morgan |
| 5,849,012 A | 12/1998 | Abboudi | | 6,019,767 A | 2/2000 | Howell |
| 5,860,973 A | 1/1999 | Michelson | | 6,022,352 A | 2/2000 | Vandewalle |
| 5,860,978 A | 1/1999 | McDevitt et al. | | 6,022,373 A | 2/2000 | Li |
| 5,868,740 A | 2/1999 | LeVeen et al. | | 6,024,758 A | 2/2000 | Thal |
| 5,868,748 A | 2/1999 | Burke | | 6,027,523 A | 2/2000 | Schmieding |
| 5,868,789 A | 2/1999 | Huebner | | 6,030,410 A | 2/2000 | Zurbrugg |
| 5,871,484 A | 2/1999 | Spievack et al. | | 6,033,429 A | 3/2000 | Magovern |
| 5,871,486 A | 2/1999 | Huebner et al. | | 6,033,430 A | 3/2000 | Bonutti |
| 5,871,490 A | 2/1999 | Schulze et al. | | 6,039,753 A | 3/2000 | Meislin |
| 5,885,294 A | 3/1999 | Pedlick et al. | | 6,041,485 A | 3/2000 | Pedlick et al. |
| 5,891,168 A | 4/1999 | Thal | | 6,042,601 A | 3/2000 | Smith |
| 5,893,592 A | 4/1999 | Schulze et al. | | 6,045,551 A | 4/2000 | Bonutti |
| 5,895,395 A | 4/1999 | Yeung | | 6,045,571 A | 4/2000 | Hill et al. |
| 5,897,564 A | 4/1999 | Schulze et al. | | 6,045,572 A | 4/2000 | Johnson et al. |
| 5,897,574 A | 4/1999 | Bonutti | | 6,045,573 A | 4/2000 | Wenstrom, Jr. et al. |
| 5,899,902 A | 5/1999 | Brown et al. | | 6,045,574 A | 4/2000 | Thal |
| 5,899,938 A | 5/1999 | Sklar et al. | | 6,047,826 A | 4/2000 | Kalinski et al. |
| 5,908,421 A | 6/1999 | Beger et al. | | 6,048,343 A | 4/2000 | Mathis et al. |
| 5,908,436 A | 6/1999 | Cuschieri et al. | | 6,051,006 A | 4/2000 | Shluzas et al. |
| 5,910,148 A | 6/1999 | Reimels et al. | | 6,051,007 A | 4/2000 | Hogendijk et al. |
| 5,911,721 A | 6/1999 | Nicholson et al. | | 6,053,916 A | 4/2000 | Moore |
| 5,918,604 A | 7/1999 | Whelan | | 6,053,921 A | 4/2000 | Wagner et al. |
| 5,921,986 A | 7/1999 | Bonutti | | 6,056,752 A | 5/2000 | Roger |
| 5,925,008 A | 7/1999 | Douglas | | 6,056,772 A | 5/2000 | Bonutti |
| 5,928,231 A | 7/1999 | Klein et al. | | 6,056,773 A | 5/2000 | Bonutti |
| 5,928,267 A | 7/1999 | Bonutti et al. | | 6,059,817 A | 5/2000 | Bonutti et al. |
| RE36,289 E | 8/1999 | Le et al. | | 6,059,818 A | 5/2000 | Johnson et al. |
| 5,931,838 A | 8/1999 | Vito | | 6,062,344 A | 5/2000 | Okabe et al. |
| 5,931,844 A | 8/1999 | Thompson et al. | | 6,066,173 A | 5/2000 | McKernan et al. |
| 5,931,869 A | 8/1999 | Boucher et al. | | 6,068,648 A | 5/2000 | Cole et al. |
| 5,935,119 A | 8/1999 | Guy et al. | | 6,071,305 A | 6/2000 | Brown et al. |
| 5,935,133 A | 8/1999 | Wagner et al. | | 6,074,403 A | 6/2000 | Nord |
| 5,935,149 A | 8/1999 | Ek | | 6,077,277 A | 6/2000 | Mollenauer et al. |

| Patent No. | Date | Inventor |
|---|---|---|
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson et al. |

| Patent No. | Date | Inventor |
|---|---|---|
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |

| | | |
|---|---|---|
| 7,172,626 B1 | 2/2007 | Andrews |
| 7,201,722 B2 | 4/2007 | Krueger |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,162,997 B2 | 4/2012 | Struhl |
| 8,167,906 B2 | 5/2012 | Cauldwell et al. |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,409,253 B2 | 4/2013 | Stone et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |

| | | | | | | |
|---|---|---|---|---|---|---|
| 2003/0176919 A1 | 9/2003 | Schmieding | | 2005/0085819 A1 | 4/2005 | Ellis et al. |
| 2003/0176920 A1 | 9/2003 | Sklar et al. | | 2005/0090828 A1 | 4/2005 | Alford |
| 2003/0181925 A1 | 9/2003 | Bain et al. | | 2005/0090862 A1 | 4/2005 | McDevitt et al. |
| 2003/0195528 A1 | 10/2003 | Ritchart | | 2005/0096696 A1 | 5/2005 | Forsberg |
| 2003/0195564 A1 | 10/2003 | Tran et al. | | 2005/0096697 A1 | 5/2005 | Forsberg et al. |
| 2003/0208210 A1 | 11/2003 | Dreyfuss et al. | | 2005/0096743 A1 | 5/2005 | Schmieding et al. |
| 2003/0212456 A1 | 11/2003 | Lipchitz et al. | | 2005/0101957 A1 | 5/2005 | Buskirk et al. |
| 2003/0220660 A1 | 11/2003 | Kortenbach et al. | | 2005/0107795 A1 | 5/2005 | Morris et al. |
| 2003/0225459 A1 | 12/2003 | Hammer et al. | | 2005/0107828 A1 | 5/2005 | Reese |
| 2003/0229396 A1 | 12/2003 | Andrews | | 2005/0119531 A1 | 6/2005 | Sharratt |
| 2004/0002734 A1 | 1/2004 | Fallin et al. | | 2005/0119696 A1 | 6/2005 | Walters et al. |
| 2004/0006345 A1 | 1/2004 | Vlahos et al. | | 2005/0124996 A1 | 6/2005 | Hearn |
| 2004/0006346 A1 | 1/2004 | Holmen et al. | | 2005/0125031 A1 | 6/2005 | Pipenhagen et al. |
| 2004/0015171 A1 | 1/2004 | Bojarski et al. | | 2005/0125036 A1 | 6/2005 | Roby |
| 2004/0015172 A1 | 1/2004 | Biedermann et al. | | 2005/0125073 A1 | 6/2005 | Orban et al. |
| 2004/0024456 A1 | 2/2004 | Brown et al. | | 2005/0131413 A1 | 6/2005 | O'Driscoll et al. |
| 2004/0024457 A1 | 2/2004 | Boyce et al. | | 2005/0137600 A1 | 6/2005 | Jacobs et al. |
| 2004/0039389 A1 | 2/2004 | West et al. | | 2005/0137624 A1 | 6/2005 | Fallman |
| 2004/0044391 A1 | 3/2004 | Porter | | 2005/0149033 A1 | 7/2005 | McGuire et al. |
| 2004/0059357 A1 | 3/2004 | Koseki | | 2005/0149122 A1 | 7/2005 | McDevitt et al. |
| 2004/0087981 A1 | 5/2004 | Berube et al. | | 2005/0149187 A1 | 7/2005 | Clark et al. |
| 2004/0092936 A1 | 5/2004 | Miller et al. | | 2005/0159812 A1 | 7/2005 | Dinger et al. |
| 2004/0093031 A1 | 5/2004 | Burkhart et al. | | 2005/0165416 A1 | 7/2005 | Bojarski et al. |
| 2004/0093032 A1 | 5/2004 | Sinnott et al. | | 2005/0165482 A1 | 7/2005 | Goldhahn et al. |
| 2004/0098051 A1 | 5/2004 | Fallin et al. | | 2005/0171603 A1 | 8/2005 | Justin et al. |
| 2004/0098053 A1 | 5/2004 | Tran | | 2005/0187565 A1 | 8/2005 | Baker et al. |
| 2004/0111117 A1 | 6/2004 | Colleran et al. | | 2005/0187577 A1 | 8/2005 | Selvitelli et al. |
| 2004/0122431 A1 | 6/2004 | Biedermann et al. | | 2005/0187635 A1 | 8/2005 | Metzger |
| 2004/0133206 A1 | 7/2004 | Stevens et al. | | 2005/0203620 A1 | 9/2005 | Steiner et al. |
| 2004/0133211 A1 | 7/2004 | Raskin et al. | | 2005/0222618 A1 | 10/2005 | Dreyfuss et al. |
| 2004/0138664 A1 | 7/2004 | Bowman | | 2005/0222619 A1 | 10/2005 | Dreyfuss et al. |
| 2004/0138683 A1 | 7/2004 | Shelton et al. | | 2005/0228448 A1 | 10/2005 | Li |
| 2004/0138704 A1 | 7/2004 | Gambale et al. | | 2005/0240198 A1 | 10/2005 | Albertson et al. |
| 2004/0138706 A1 | 7/2004 | Abrams et al. | | 2005/0251159 A1 | 11/2005 | Ewers et al. |
| 2004/0138747 A1 | 7/2004 | Kaladelfos | | 2005/0251177 A1 | 11/2005 | Saadat et al. |
| 2004/0143344 A1 | 7/2004 | Malaviya et al. | | 2005/0251208 A1 | 11/2005 | Elmer et al. |
| 2004/0147932 A1 | 7/2004 | Burkinshaw et al. | | 2005/0251210 A1 | 11/2005 | Westra et al. |
| 2004/0147958 A1 | 7/2004 | Lam et al. | | 2005/0267479 A1 | 12/2005 | Morgan et al. |
| 2004/0153103 A1 | 8/2004 | Schwartz et al. | | 2005/0267533 A1 | 12/2005 | Gertner |
| 2004/0153153 A1 | 8/2004 | Elson et al. | | 2005/0277939 A1 | 12/2005 | Miller |
| 2004/0162579 A1 | 8/2004 | Foerster | | 2005/0277961 A1 | 12/2005 | Stone et al. |
| 2004/0166169 A1 | 8/2004 | Malaviya et al. | | 2005/0283040 A1 | 12/2005 | Greenhalgh |
| 2004/0182968 A1 | 9/2004 | Gentry | | 2005/0283156 A1 | 12/2005 | Schmieding et al. |
| 2004/0187314 A1 | 9/2004 | Johnson | | 2005/0283158 A1 | 12/2005 | West |
| 2004/0199169 A1 | 10/2004 | Koons et al. | | 2005/0283192 A1 | 12/2005 | Torrie et al. |
| 2004/0204722 A1 | 10/2004 | Sikora et al. | | 2006/0004410 A1 | 1/2006 | Nobis et al. |
| 2004/0220574 A1 | 11/2004 | Pelo et al. | | 2006/0015103 A1 | 1/2006 | Burke |
| 2004/0225292 A1 | 11/2004 | Sasso et al. | | 2006/0015106 A1 | 1/2006 | Lerch et al. |
| 2004/0225305 A1 | 11/2004 | Ewers et al. | | 2006/0015107 A1 | 1/2006 | Sklar |
| 2004/0236353 A1 | 11/2004 | Bain et al. | | 2006/0030884 A1 | 2/2006 | Yeung et al. |
| 2004/0236373 A1 | 11/2004 | Anspach | | 2006/0030948 A1 | 2/2006 | Manrique et al. |
| 2004/0243139 A1 | 12/2004 | Lewis et al. | | 2006/0036265 A1 | 2/2006 | Dant |
| 2004/0243178 A1 | 12/2004 | Haut et al. | | 2006/0052787 A1 | 3/2006 | Re et al. |
| 2004/0243235 A1 | 12/2004 | Goh et al. | | 2006/0052818 A1 | 3/2006 | Drake et al. |
| 2004/0249394 A1 | 12/2004 | Morris et al. | | 2006/0064125 A1 | 3/2006 | Henderson et al. |
| 2004/0260296 A1 | 12/2004 | Kaiser et al. | | 2006/0064126 A1 | 3/2006 | Fallin et al. |
| 2004/0260298 A1 | 12/2004 | Kaiser et al. | | 2006/0069334 A1 | 3/2006 | Moskowitz |
| 2004/0267164 A1 | 12/2004 | Rhodes et al. | | 2006/0079904 A1 | 4/2006 | Thal |
| 2004/0267265 A1 | 12/2004 | Kyle | | 2006/0084943 A1 | 4/2006 | Rosenman et al. |
| 2004/0267270 A1 | 12/2004 | Jacobs et al. | | 2006/0085000 A1 | 4/2006 | Mohr et al. |
| 2004/0267276 A1 | 12/2004 | Camino et al. | | 2006/0089672 A1 | 4/2006 | Martinek |
| 2004/0267277 A1 | 12/2004 | Zannis et al. | | 2006/0095130 A1 | 5/2006 | Caborn et al. |
| 2004/0267286 A1 | 12/2004 | Gao et al. | | 2006/0095131 A1 | 5/2006 | Justin et al. |
| 2004/0267304 A1 | 12/2004 | Zannis et al. | | 2006/0100627 A1 | 5/2006 | Stone et al. |
| 2004/0267309 A1 | 12/2004 | Garvin | | 2006/0100637 A1 | 5/2006 | Rathbun et al. |
| 2004/0267361 A1 | 12/2004 | Donnelly et al. | | 2006/0106423 A1 | 5/2006 | Weisel et al. |
| 2004/0267362 A1 | 12/2004 | Hwang et al. | | 2006/0111721 A1 | 5/2006 | Puricelli et al. |
| 2005/0021087 A1 | 1/2005 | Koseki | | 2006/0116685 A1 | 6/2006 | Urbanski et al. |
| 2005/0027307 A1 | 2/2005 | Schwartz et al. | | 2006/0121084 A1 | 6/2006 | Borden et al. |
| 2005/0033363 A1 | 2/2005 | Bojarski et al. | | 2006/0122611 A1 | 6/2006 | Morales et al. |
| 2005/0038426 A1 | 2/2005 | Chan | | 2006/0135958 A1 | 6/2006 | Marissen et al. |
| 2005/0055027 A1 | 3/2005 | Yeung et al. | | 2006/0149258 A1 | 7/2006 | Sousa |
| 2005/0055037 A1 | 3/2005 | Fathauer | | 2006/0149266 A1 | 7/2006 | Cordasco |
| 2005/0064042 A1 | 3/2005 | Vunjak-Novakovic et al. | | 2006/0155287 A1 | 7/2006 | Montgomery et al. |
| 2005/0065521 A1 | 3/2005 | Steger et al. | | 2006/0161161 A1 | 7/2006 | Shifrin et al. |
| 2005/0065526 A1 | 3/2005 | Drew et al. | | 2006/0167458 A1 | 7/2006 | Gabele |
| 2005/0070906 A1 | 3/2005 | Clark et al. | | 2006/0167481 A1 | 7/2006 | Baker et al. |
| 2005/0070928 A1 | 3/2005 | Heino et al. | | 2006/0167482 A1 | 7/2006 | Swain et al. |
| 2005/0074495 A1 | 4/2005 | Schwartz et al. | | 2006/0173492 A1 | 8/2006 | Akerfeldt et al. |

| | | | | | | |
|---|---|---|---|---|---|---|
| 2006/0178680 A1 | 8/2006 | Nelson et al. | | 2008/0140128 A1 | 6/2008 | Smisson et al. |
| 2006/0189993 A1 | 8/2006 | Stone | | 2008/0154260 A1 | 6/2008 | Hoof |
| 2006/0190042 A1 | 8/2006 | Stone et al. | | 2008/0154314 A1 | 6/2008 | McDevitt |
| 2006/0195101 A1 | 8/2006 | Stevens | | 2008/0161806 A1 | 7/2008 | Donnelly et al. |
| 2006/0200235 A1 | 9/2006 | Bianchi et al. | | 2008/0161852 A1 | 7/2008 | Kaiser et al. |
| 2006/0212055 A1 | 9/2006 | Karabey et al. | | 2008/0161861 A1 | 7/2008 | Huebner |
| 2006/0229671 A1 | 10/2006 | Steiner et al. | | 2008/0161864 A1 | 7/2008 | Beck et al. |
| 2006/0235407 A1 | 10/2006 | Wang et al. | | 2008/0172097 A1 | 7/2008 | Lerch et al. |
| 2006/0235413 A1 | 10/2006 | Denham et al. | | 2008/0183290 A1 | 7/2008 | Baird et al. |
| 2006/0241624 A1 | 10/2006 | Kizuka et al. | | 2008/0188933 A1 | 8/2008 | Koob et al. |
| 2006/0247642 A1 | 11/2006 | Stone et al. | | 2008/0188936 A1 | 8/2008 | Ball et al. |
| 2006/0253130 A1 | 11/2006 | Wolniewicz | | 2008/0221527 A1 | 9/2008 | Bradley et al. |
| 2006/0259048 A1 | 11/2006 | Koseki | | 2008/0221578 A1 | 9/2008 | Zeitani |
| 2006/0271192 A1 | 11/2006 | Olsen et al. | | 2008/0228186 A1 | 9/2008 | Gall et al. |
| 2006/0276793 A1 | 12/2006 | Berry | | 2008/0234730 A1 | 9/2008 | Cotton et al. |
| 2006/0276809 A1 | 12/2006 | Oliveira | | 2008/0255613 A1 | 10/2008 | Kaiser et al. |
| 2006/0276841 A1 | 12/2006 | Barbieri et al. | | 2008/0262544 A1 | 10/2008 | Burkhart |
| 2006/0280768 A1 | 12/2006 | Hwang et al. | | 2008/0268064 A1 | 10/2008 | Woodell-May |
| 2006/0282082 A1 | 12/2006 | Fanton et al. | | 2008/0269674 A1 | 10/2008 | Stone |
| 2006/0282083 A1 | 12/2006 | Fanton et al. | | 2008/0275477 A1 | 11/2008 | Sterrett et al. |
| 2006/0282085 A1 | 12/2006 | Stone et al. | | 2008/0312689 A1 | 12/2008 | Denham et al. |
| 2006/0293709 A1 | 12/2006 | Bojarski et al. | | 2009/0018589 A1 | 1/2009 | Smisson, III et al. |
| 2007/0005080 A1 | 1/2007 | Wolniewicz et al. | | 2009/0018655 A1 | 1/2009 | Brunelle et al. |
| 2007/0010857 A1 | 1/2007 | Sugimoto et al. | | 2009/0043342 A1 | 2/2009 | Freedland |
| 2007/0016305 A1 | 1/2007 | Chudik | | 2009/0054928 A1 | 2/2009 | Denham et al. |
| 2007/0021779 A1 | 1/2007 | Garvin et al. | | 2009/0062854 A1 | 3/2009 | Kaiser et al. |
| 2007/0032800 A1 | 2/2007 | Ortiz et al. | | 2009/0082790 A1 | 3/2009 | Shad et al. |
| 2007/0038218 A1 | 2/2007 | Grevious | | 2009/0082805 A1 | 3/2009 | Kaiser et al. |
| 2007/0043371 A1 | 2/2007 | Teague et al. | | 2009/0099598 A1 | 4/2009 | McDevitt et al. |
| 2007/0055249 A1 | 3/2007 | Jensen et al. | | 2009/0105754 A1 | 4/2009 | Sethi |
| 2007/0055251 A1 | 3/2007 | Huebner et al. | | 2009/0118774 A1 | 5/2009 | Miller, III |
| 2007/0055255 A1 | 3/2007 | Siegel | | 2009/0118775 A1 | 5/2009 | Burke |
| 2007/0060922 A1 | 3/2007 | Dreyfuss | | 2009/0125073 A1 | 5/2009 | Rehm |
| 2007/0067025 A1 | 3/2007 | Schwartz | | 2009/0138002 A1 | 5/2009 | Fenton |
| 2007/0073307 A1 | 3/2007 | Scribner et al. | | 2009/0138054 A1 | 5/2009 | Teague et al. |
| 2007/0078435 A1 | 4/2007 | Stone et al. | | 2009/0156997 A1 | 6/2009 | Trenhaile |
| 2007/0083236 A1 | 4/2007 | Sikora et al. | | 2009/0163949 A1 | 6/2009 | Rolnick et al. |
| 2007/0093847 A1 | 4/2007 | Scribner et al. | | 2009/0177233 A1 | 7/2009 | Malek |
| 2007/0100350 A1 | 5/2007 | Deffenbaugh et al. | | 2009/0192468 A1 | 7/2009 | Stone |
| 2007/0118217 A1 | 5/2007 | Brulez et al. | | 2009/0198277 A1 | 8/2009 | Gordon et al. |
| 2007/0123883 A1 | 5/2007 | Ellis et al. | | 2009/0204146 A1 | 8/2009 | Kaiser et al. |
| 2007/0142838 A1 | 6/2007 | Jordan | | 2009/0228042 A1 | 9/2009 | Koogle,, Jr. et al. |
| 2007/0156174 A1 | 7/2007 | Kaiser et al. | | 2009/0234357 A1 | 9/2009 | Morales et al. |
| 2007/0162018 A1 | 7/2007 | Jensen et al. | | 2009/0234358 A1 | 9/2009 | Morales et al. |
| 2007/0185488 A1 | 8/2007 | Pohjonen et al. | | 2009/0240251 A1 | 9/2009 | Gabele |
| 2007/0185532 A1 | 8/2007 | Stone et al. | | 2009/0240335 A1 | 9/2009 | Arcenio et al. |
| 2007/0185568 A1 | 8/2007 | Schwartz | | 2009/0248091 A1 | 10/2009 | Teague et al. |
| 2007/0191849 A1 | 8/2007 | ElAttrache et al. | | 2009/0265014 A1 | 10/2009 | May et al. |
| 2007/0191853 A1 | 8/2007 | Stone | | 2009/0299409 A1 | 12/2009 | Coe et al. |
| 2007/0198036 A1 | 8/2007 | Sklar et al. | | 2009/0306711 A1 | 12/2009 | Stone et al. |
| 2007/0219558 A1 | 9/2007 | Deutsch | | 2009/0312776 A1 | 12/2009 | Kaiser et al. |
| 2007/0225719 A1 | 9/2007 | Stone et al. | | 2009/0318960 A1 | 12/2009 | Burkhart |
| 2007/0225805 A1 | 9/2007 | Schmieding | | 2009/0318961 A1 | 12/2009 | Stone et al. |
| 2007/0233241 A1 | 10/2007 | Graf et al. | | 2010/0042114 A1 | 2/2010 | Schaffhausen |
| 2007/0239209 A1 | 10/2007 | Fallman | | 2010/0087857 A1 | 4/2010 | Stone et al. |
| 2007/0239275 A1 | 10/2007 | Willobee | | 2010/0145384 A1 | 6/2010 | Stone et al. |
| 2007/0250163 A1 | 10/2007 | Cassani | | 2010/0191342 A1 | 7/2010 | Byrd et al. |
| 2007/0260251 A1 | 11/2007 | Weier et al. | | 2010/0211075 A1 | 8/2010 | Stone |
| 2007/0260279 A1 | 11/2007 | Hotter et al. | | 2010/0256677 A1 | 10/2010 | Albertorio et al. |
| 2007/0270856 A1 | 11/2007 | Morales et al. | | 2010/0268273 A1 | 10/2010 | Albertorio et al. |
| 2007/0276387 A1 | 11/2007 | Morales et al. | | 2010/0268275 A1 | 10/2010 | Stone et al. |
| 2008/0027430 A1 | 1/2008 | Montgomery et al. | | 2010/0270306 A1 | 10/2010 | Shiffer |
| 2008/0027446 A1 | 1/2008 | Stone et al. | | 2010/0292792 A1 | 11/2010 | Stone et al. |
| 2008/0033549 A1 | 2/2008 | Marshall et al. | | 2010/0305698 A1 | 12/2010 | Metzger et al. |
| 2008/0046009 A1 | 2/2008 | Albertorio et al. | | 2010/0305709 A1 | 12/2010 | Metzger et al. |
| 2008/0051836 A1 | 2/2008 | Foerster et al. | | 2010/0312341 A1 | 12/2010 | Kaiser et al. |
| 2008/0065114 A1 | 3/2008 | Stone et al. | | 2011/0009885 A1 | 1/2011 | Graf et al. |
| 2008/0071299 A1 | 3/2008 | Allinniemi et al. | | 2011/0046733 A1 | 2/2011 | Eggli |
| 2008/0082101 A1 | 4/2008 | Reisberg | | 2011/0087284 A1 | 4/2011 | Stone et al. |
| 2008/0082127 A1 | 4/2008 | Stone et al. | | 2011/0098727 A1 | 4/2011 | Kaiser et al. |
| 2008/0082128 A1 | 4/2008 | Stone | | 2011/0106153 A1 | 5/2011 | Stone et al. |
| 2008/0097430 A1 | 4/2008 | Bernstein et al. | | 2011/0160767 A1 | 6/2011 | Stone et al. |
| 2008/0119892 A1 | 5/2008 | Brailovski et al. | | 2011/0160768 A1 | 6/2011 | Stone et al. |
| 2008/0132753 A1 | 6/2008 | Goddard | | 2011/0208239 A1 | 8/2011 | Stone et al. |
| 2008/0132932 A1 | 6/2008 | Hoeppner et al. | | 2011/0208240 A1 | 8/2011 | Stone et al. |
| 2008/0132948 A1 | 6/2008 | Surti et al. | | 2011/0213416 A1 | 9/2011 | Kaiser |
| 2008/0133007 A1 | 6/2008 | Donnelly et al. | | 2011/0218625 A1 | 9/2011 | Berelsman et al. |
| 2008/0140092 A1 | 6/2008 | Stone et al. | | 2011/0264141 A1 | 10/2011 | Denham et al. |
| 2008/0140093 A1 | 6/2008 | Stone et al. | | 2011/0270278 A1 | 11/2011 | Overes et al. |

| | | | | | | |
|---|---|---|---|---|---|---|
| 2011/0270306 A1 | 11/2011 | Denham et al. | | EP | 0582514 | 2/1994 |
| 2012/0041485 A1 | 2/2012 | Kaiser et al. | | EP | 0591991 | 4/1994 |
| 2012/0041486 A1 | 2/2012 | Stone et al. | | EP | 0598219 | 5/1994 |
| 2012/0046693 A1 | 2/2012 | Denham et al. | | EP | 0611551 A1 | 8/1994 |
| 2012/0053630 A1 | 3/2012 | Denham et al. | | EP | 0627203 | 12/1994 |
| 2012/0059417 A1 | 3/2012 | Norton et al. | | EP | 0651979 | 5/1995 |
| 2012/0059418 A1 | 3/2012 | Denham et al. | | EP | 0669110 | 8/1995 |
| 2012/0089193 A1 | 4/2012 | Stone et al. | | EP | 0686373 | 12/1995 |
| 2012/0095470 A1 | 4/2012 | Kaiser et al. | | EP | 0702933 | 3/1996 |
| 2012/0123474 A1 | 5/2012 | Zajac et al. | | EP | 0775473 | 5/1997 |
| 2012/0123541 A1 | 5/2012 | Albertorio et al. | | EP | 0913123 | 5/1999 |
| 2012/0150297 A1 | 6/2012 | Denham et al. | | EP | 0913131 | 5/1999 |
| 2012/0165866 A1 | 6/2012 | Kaiser et al. | | EP | 99121106 | 10/1999 |
| 2012/0165867 A1 | 6/2012 | Denham et al. | | EP | 991210527 | 10/1999 |
| 2012/0165938 A1 | 6/2012 | Denham et al. | | EP | 0995409 | 4/2000 |
| 2012/0197271 A1 | 8/2012 | Astorino et al. | | EP | 1013229 | 6/2000 |
| 2012/0245585 A1 | 9/2012 | Kaiser et al. | | EP | 1093773 | 4/2001 |
| 2012/0296427 A1 | 11/2012 | Conner et al. | | EP | 1093774 | 4/2001 |
| 2012/0310245 A1 | 12/2012 | Hoeppner et al. | | EP | 1555945 | 7/2005 |
| 2013/0023930 A1 | 1/2013 | Stone et al. | | EP | 2238944 A2 | 10/2010 |
| 2013/0035698 A1 | 2/2013 | Stone et al. | | EP | 2544607 A1 | 1/2013 |
| 2013/0046341 A1 | 2/2013 | Stone et al. | | FR | 2622790 | 5/1989 |
| 2013/0103082 A1 | 4/2013 | Kaiser et al. | | FR | 2655840 | 6/1991 |
| 2013/0110251 A1 | 5/2013 | Metzger et al. | | FR | 2682867 | 4/1993 |
| 2013/0116730 A1 | 5/2013 | Denham et al. | | FR | 2687911 | 9/1993 |
| 2013/0123813 A1 | 5/2013 | Stone et al. | | FR | 2688689 | 9/1993 |
| | | | | FR | 2704140 | 10/1994 |
| FOREIGN PATENT DOCUMENTS | | | | FR | 2717070 | 9/1995 |
| | | | | FR | 2723528 | 2/1996 |
| AU | 4957264 | 3/1966 | | FR | 2744010 | 8/1997 |
| AU | 440266 | 10/1967 | | FR | 2745999 | 9/1997 |
| AU | 5850469 | 1/1971 | | FR | 2770764 | 5/1999 |
| AU | 5963869 | 2/1971 | | GB | 401677 | 11/1933 |
| AU | 1505470 | 11/1971 | | GB | 1413477 | 11/1975 |
| AU | 2223767 | 5/1973 | | GB | 1485681 | 9/1977 |
| AU | 3615171 | 5/1973 | | GB | 2083751 | 3/1982 |
| AU | 5028569 | 9/1973 | | GB | 2118474 | 11/1983 |
| AU | 7110887 | 10/1987 | | GB | 2227175 | 7/1990 |
| AU | 639410 | 11/1989 | | GB | 2253147 A | 9/1992 |
| AU | 651929 | 8/1994 | | GB | 2312376 | 10/1997 |
| DE | 2529669 | 3/1976 | | GB | 2403416 A | 1/2005 |
| DE | 2747312 | 4/1979 | | JP | 5362911 | 5/1978 |
| DE | 2818254 | 10/1979 | | JP | 5362912 | 5/1978 |
| DE | 2919009 | 11/1979 | | JP | 5374942 | 6/1978 |
| DE | 3027138 | 12/1981 | | JP | 5378230 | 6/1978 |
| DE | 3225620 | 2/1983 | | JP | 62159647 | 7/1987 |
| DE | 3136083 | 3/1983 | | JP | 62295657 | 12/1987 |
| DE | 233303 | 2/1986 | | JP | 5269160 | 10/1993 |
| DE | 4127550 | 2/1993 | | JP | 5300917 | 11/1993 |
| DE | 4302397 | 7/1993 | | JP | 751292 | 2/1995 |
| DE | 29621340 | 5/1998 | | JP | 10211213 | 8/1998 |
| DE | 19841252 | 3/2000 | | WO | WO-8300615 | 3/1983 |
| DE | 20207781 U1 | 8/2002 | | WO | WO-8603666 | 7/1986 |
| EP | 0108912 | 5/1984 | | WO | WO-8701270 | 3/1987 |
| EP | 0129442 | 12/1984 | | WO | WO-8901767 | 3/1989 |
| EP | 0172130 | 2/1986 | | WO | WO-8909030 | 10/1989 |
| EP | 0241240 | 10/1987 | | WO | WO-8910096 | 11/1989 |
| EP | 0241792 | 10/1987 | | WO | WO-9008510 | 8/1990 |
| EP | 0260970 | 3/1988 | | WO | WO-9203980 | 3/1992 |
| EP | 0270704 | 6/1988 | | WO | WO-9314705 | 8/1993 |
| EP | 0282789 | 9/1988 | | WO | WO-9315694 | 8/1993 |
| EP | 0315371 | 5/1989 | | WO | WO-9502373 | 1/1995 |
| EP | 0317406 | 5/1989 | | WO | WO-9503003 | 2/1995 |
| EP | 0340159 | 11/1989 | | WO | WO-9529637 | 11/1995 |
| EP | 0346183 | 12/1989 | | WO | WO-9532670 | 12/1995 |
| EP | 0349173 | 1/1990 | | WO | WO-9609797 A1 | 4/1996 |
| EP | 0374088 | 6/1990 | | WO | WO-9629029 | 9/1996 |
| EP | 0409364 | 1/1991 | | WO | WO-9737603 | 10/1997 |
| EP | 0415915 | 3/1991 | | WO | WO-9812991 | 4/1998 |
| EP | 0440991 | 8/1991 | | WO | WO-9812992 | 4/1998 |
| EP | 0441065 | 8/1991 | | WO | WO-9822047 | 5/1998 |
| EP | 0451932 | 10/1991 | | WO | WO-9822048 | 5/1998 |
| EP | 0464480 | 1/1992 | | WO | WO-9901084 | 1/1999 |
| EP | 0497079 | 8/1992 | | WO | WO-9912480 | 3/1999 |
| EP | 0502509 | 9/1992 | | WO | WO-9937219 A1 | 7/1999 |
| EP | 0502698 | 9/1992 | | WO | WO-9944544 | 9/1999 |
| EP | 520177 | 12/1992 | | WO | WO-9952472 A1 | 10/1999 |
| EP | 0546726 | 6/1993 | | WO | WO-0040159 | 7/2000 |
| EP | 0574707 | 12/1993 | | WO | WO-0139671 | 6/2001 |

| | | |
|---|---|---|
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2006023661 A2 | 3/2006 |
| WO | WO-2006055823 A2 | 5/2006 |
| WO | WO-2007045460 A2 | 4/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |

OTHER PUBLICATIONS

US 6,238,418, 05/2001, Schwartz et al. (withdrawn).
"AperFix® System Surgical Technique Guide. Single Tunnel Double Bundle.™" Cayenne Medical brochure. (Aug. 2008) 8 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 , Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
"Arthroscopic Meniscal Repair using the Meniscal Cinch™", Surgical Technique brochure. (2008) Artherex® 6 sheets.
Pioneer® Sternal Cable System (2010).
Rapid Sternal Closeure (2006) KLS Martin L.P. http://www.rapidsternalclosure.com/medical/demp.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J> v.33(4); (2006).
Zeitani, Jacob, M.D., "A New Sternal Reinforcement Device to Prevent and Treat Sternal Dehiscence," CTSNet.org (Jun. 30, 2008).
Invitation to Pay Additional Fees mailed Jul. 19, 2012, for PCT/US2012/037703 claiming benefit of U.S. Appl. No. 13/109,667, filed May 7, 2011.
"Suture Tensioner w/Tensiometer," Arthrex® , Inc. catalog "Next Generation in Knee Ligament Reconstruction & Repair Technology," 2009.
"TriTis™ Tibial Fixation System and Implant" brochure. Scandius Biomedical (2006).
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.

* cited by examiner

*Primary Examiner* — Jason-Dennis Stewart
(74) *Attorney, Agent, or Firm* — Harness, Dickey

(57) ABSTRACT

A method for trochanteric reattachment can include positioning a femoral prosthesis relative to a proximal portion of a femur. A first portion of a self-locking adjustable flexible member construct can be coupled to a first attachment region of the prosthesis, and a second portion of the self-locking adjustable flexible member construct can be coupled to a second attachment region of the femoral prosthesis, where the second portion can be opposite the first portion. A trochanter can be positioned relative to the femur and a trochanteric engaging region of the prosthesis, and the self-locking adjustable flexible member construct can be positioned around an outer surface of the trochanter. Free ends of the self-locking adjustable flexible member construct can be tensioned to draw the trochanter into secure engagement with the prosthesis and the femur via the self-locking adjustable flexible member construct in an absence of a knot.

28 Claims, 14 Drawing Sheets

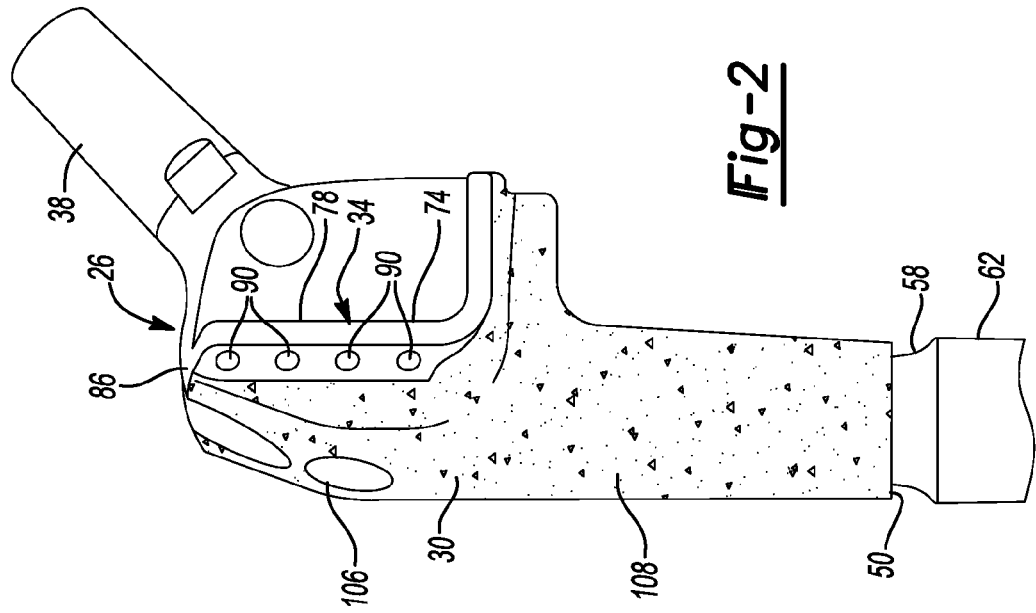
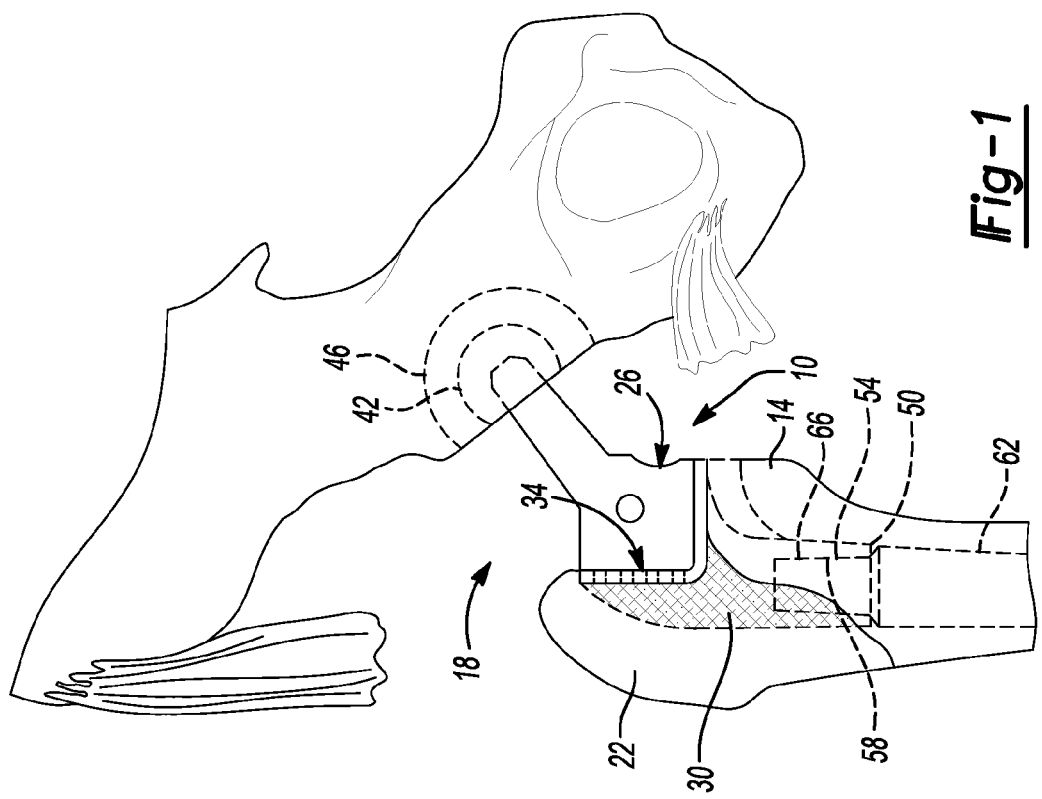

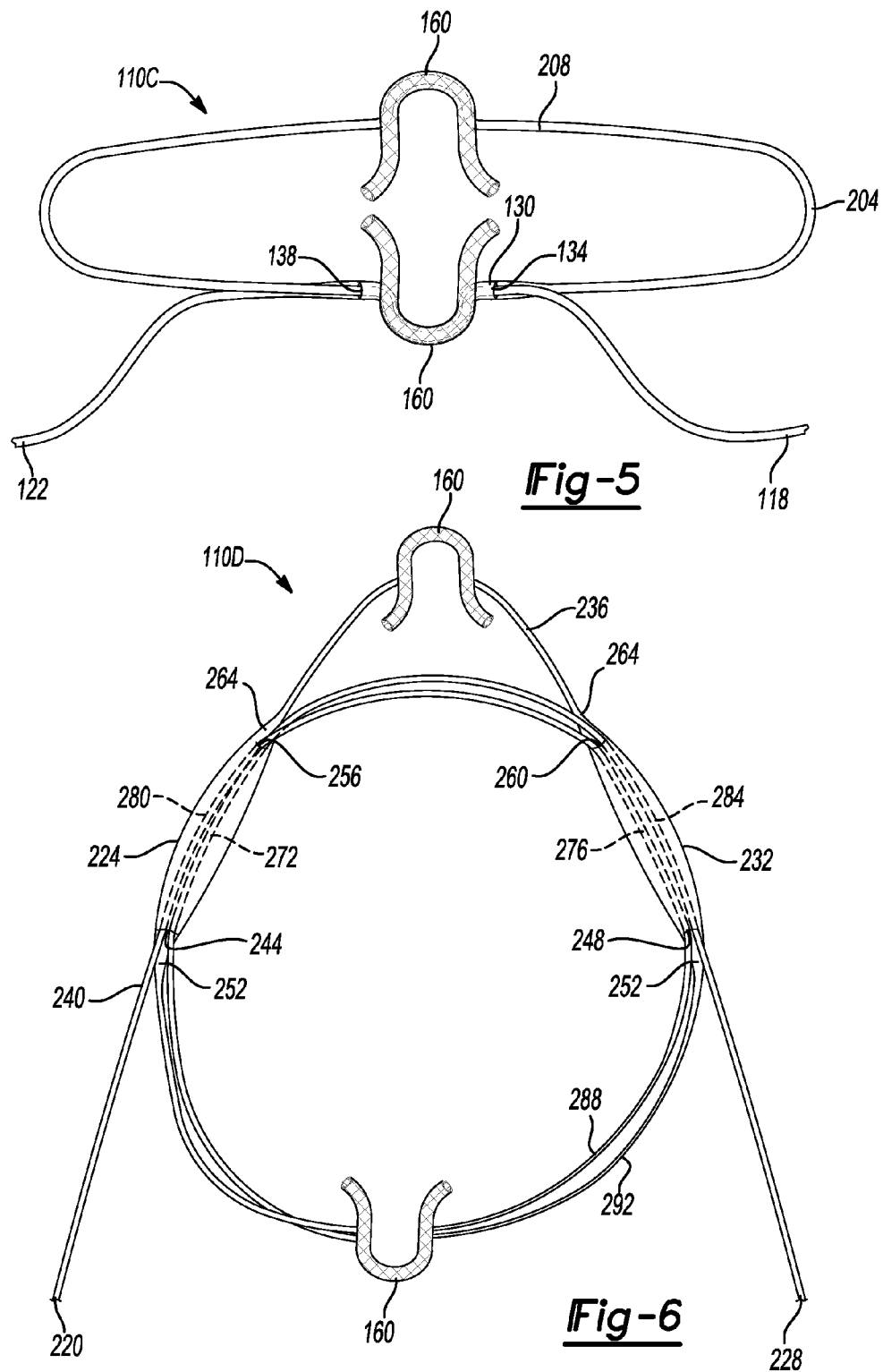

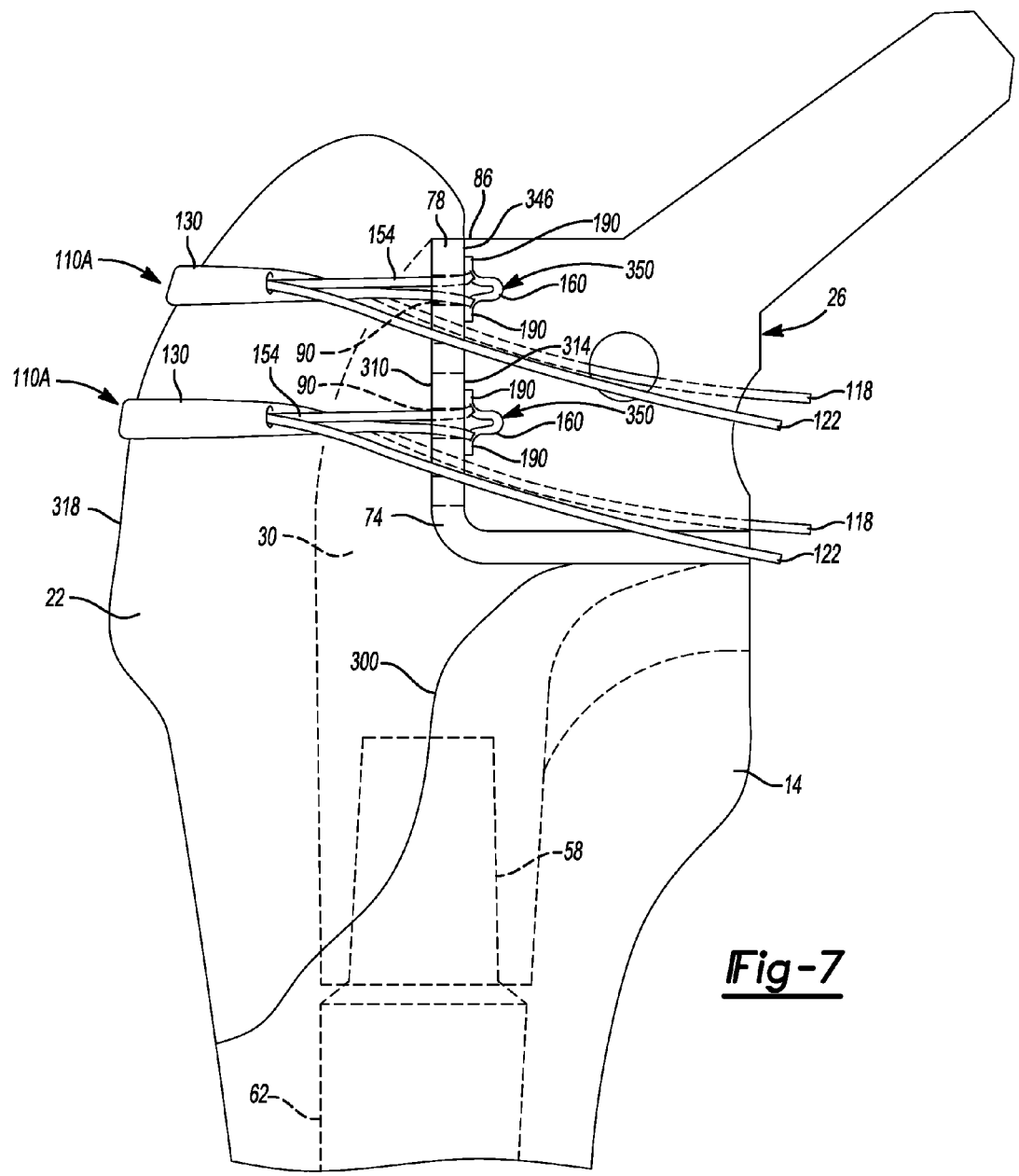

METHOD FOR TROCHANTERIC REATTACHMENT

CROSS REFERENCE TO RELATED APPLICATIONS

This application is a continuation-in-part of U.S. patent application Ser. No. 12/938,902 filed on Nov. 3, 2010, which is a continuation-in-part of U.S. patent application Ser. No. 12/915,962 filed on Oct. 29, 2010, which is a continuation-in-part of U.S. patent application Ser. No. 12/719,337 filed on Mar. 8, 2010, which is a continuation-in-part of U.S. patent application Ser. No. 12/489,168 filed on Jun. 22, 2009, which is a continuation-in-part of U.S. patent application Ser. No. 12/474,802 filed on May 29, 2009, which is a continuation-in-part of (a) U.S. patent application Ser. No. 12/196,405 filed on Aug. 22, 2008; (b) U.S. patent application Ser. No. 12/196,407 filed on Aug. 22, 2008; (c) U.S. patent application Ser. No. 12/196,410 filed on Aug. 22, 2008; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, which is a continuation-in-part of U.S. patent application Ser. No. 12/014,399 filed on Jan. 15, 2008, which is a continuation-in-part of U.S. patent application Ser. No. 11/347,661 filed on Feb. 3, 2006, which is now U.S. Pat. No. 7,749,250 issued on Jul. 6, 2010.

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 12/196,398 filed Aug. 22, 2008, which is a continuation-in-part of U.S. patent application Ser. No. 11/784,821 filed Apr. 10, 2007.

The disclosures of all of the above applications are incorporated by reference herein.

FIELD

The present disclosure relates generally to a method for securing a fractured or resected bone, and more particularly to methods for trochanteric reattachment.

BACKGROUND

The statements in this section merely provide background information related to the present disclosure and may not constitute prior art.

After trauma or surgical intervention, there may be a need to fix bone fragments or portions together to immobilize the fragments and permit healing. Compressive force can be applied to the bone fragments by encircling the bone fragments or bridging the fragments together across a broken, sectioned, resected or otherwise compromised portion of the bone. The compressive forces should be applied such that upon ingrowth of new bone, the fragments will heal together and restore strength to the site of trauma or surgical intervention.

For example, in many reconstructive procedures of the hip, the greater trochanter is often resected from the proximal femur and then retracted to permit the physician to approach the joint. After the femoral head is replaced with a prosthetic femoral component, the greater trochanter can be relocated and fastened in place. Existing methods for reattachment of the greater trochanter include the use of U-bolts, bolts, clamps, plates and screws.

While these methods work for their intended purpose, there remains a need for improved apparatus and methods to apply compressive force to a bone, such as the greater trochanter, across a fracture or other resected area to maintain alignment and assist healing. Further, there is a need for apparatus and methods that are easy to use intraoperatively to accommodate various bone sizes or shapes, or locations of bone fractures or resections.

SUMMARY

This section provides a general summary of the disclosure, and is not a comprehensive disclosure of its full scope or all of its features.

In one form, a method for trochanteric reattachment is provided in accordance with various aspects of the present teachings. The method can include positioning a femoral prosthesis relative to a proximal portion of a femur. A first portion of a self-locking adjustable flexible member construct can be coupled to a first attachment region of the femoral prosthesis, and a second portion of the self-locking adjustable flexible member construct can be coupled to a second attachment region of the femoral prosthesis, where the second portion can be opposite the first portion. A trochanter can be positioned relative to the femur and a trochanteric engaging region of the femoral prosthesis, and the self-locking adjustable flexible member construct can be positioned around an outer surface of the greater trochanter. Free ends of the self-locking adjustable flexible member construct can be tensioned to draw the trochanter into secure engagement with the femoral prosthesis and the femur via the self-locking adjustable flexible member construct in an absence of a knot.

In another form, a method for trochanteric reattachment is provided in accordance with various aspects of the present teachings. The method can include positioning a femoral prosthesis relative to a proximal portion of a femur. First and second bores can be formed spaced apart from each other and through a greater trochanter that has been at least partially separated from the femur. A first portion of a self-locking adjustable flexible member construct can be passed through the first bore, and the first portion can be coupled to a first attachment region of the femoral prosthesis. A second portion of the self-locking flexible member construct can be passed through the second bore, and the second portion can be coupled to a second attachment region of the femoral prosthesis opposite of the first attachment region. The self-locking adjustable flexible member construct can be positioned around an outer surface of the greater trochanter. Free ends of the self-locking adjustable flexible member construct can be tensioned to draw the greater trochanter into secure engagement with the femoral prosthesis and the femur via the self-locking adjustable flexible member construct in an absence of a knot.

In yet another form, a method for trochanteric reattachment is provided in accordance with various aspects of the present teachings. The method can include positioning a femoral prosthesis relative to a proximal portion of a femur, where the prosthesis can include first and second attachment regions each having a plurality of attachment members spaced apart from each other and arranged at increasing distances from a proximal end of the prosthesis toward a distal end. The first and second attachment regions can be on opposite sides of the femoral prosthesis. A first portion of a first self-locking adjustable flexible member construct can be coupled to a first attachment member of the first attachment region, and a second portion of the first self-locking adjustable flexible member construct can be coupled to a second attachment member of the second attachment region. A first portion of a second self-locking adjustable flexible member construct can be coupled to a third attachment member of the first attachment region, and a second portion of the second self-locking adjustable flexible member construct can be coupled to a fourth attachment member of the second attachment region. The first and second self-locking adjustable flexible member constructs can be positioned around an outer surface of the greater trochanter such that the first and second self-locking adjustable flexible member constructs overlap each other. Free ends of the first and second self-locking adjustable flexible member constructs can be tensioned to draw the greater trochanter into secure engagement with the femoral prosthesis and the femur via the self-locking adjustable flexible member construct in an absence of a knot.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

FIG. 1 is a partial view of the bones of an exemplary hip joint, where a proximal portion of the femur and a portion of the surrounding soft tissue have been resected and replaced with an exemplary femoral hip prosthesis in accordance with the teachings of the present disclosure;

FIG. 2 is a partial view of the exemplary femoral prosthesis of FIG. 1 having an attachment region in accordance with the teachings of the present disclosure;

FIGS. 3-6 are views of exemplary adjustable flexible member constructs having optional fasteners coupled thereto in accordance with the teachings of the present disclosure; and FIGS. 7-16 are various views depicting exemplary techniques for trochanteric reattachment using the various adjustable flexible member constructs of FIGS. 3-6 in accordance with the teachings of the present disclosure.

DETAILED DESCRIPTION

Figure 3:
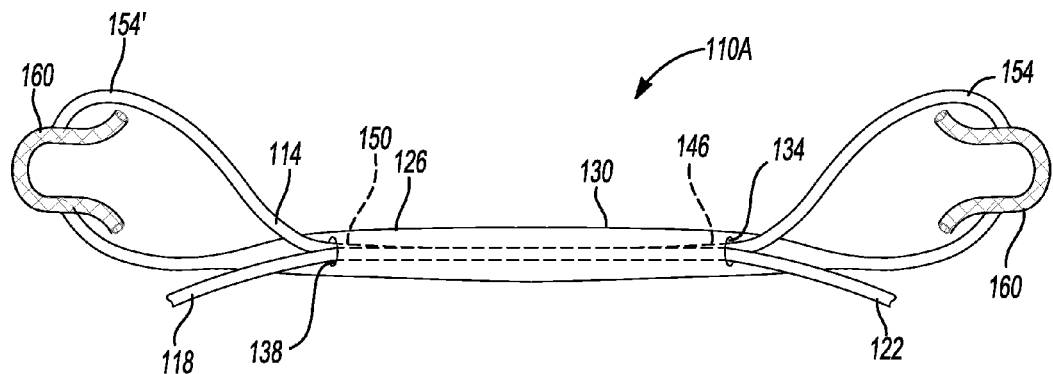

The following description is merely exemplary in nature and is not intended to limit the present disclosure, its application, or uses. It should be understood that throughout the drawings, corresponding reference numerals indicate like or corresponding parts and features. Although the following discussion is related generally to reattachment of the greater trochanter of a femur, it should be appreciated that the method and apparatus discussed herein can be applied to other bones and/or areas of the anatomy including, for example, the greater trochanter of a humerus of a shoulder joint.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

With initial reference to FIGS. 1 and 2, an exemplary proximal femoral prosthesis 10 is shown for use in replacing a portion of the proximal femur 14 in a hip joint 18. As will be discussed in greater detail below, femoral prosthesis 10 can be used for reattachment of greater trochanter 22 that has been fractured, separated, and/or resected during a hip reconstruction procedure.

In the exemplary configuration illustrated, femoral prosthesis 10 can include a proximal body 26 having a trochanteric engaging region 30 and a trochanteric attachment region 34. A tapered neck portion 38 can extend from the proximal body 26 and can be configured to mate with a femoral head 42. After implantation, femoral head 42 can be configured to mate with an implanted acetabular prosthesis 46, as shown in FIG. 1. A distal end 50 of the proximal body 26 can include a female bore 54 configured to mate with a corresponding proximal extension 58 of a distal stem 62. In one exemplary configuration, the proximal body 26 can be interconnected to the distal stem 62 via a Morse taper connection 66.

The femoral prosthesis 10 can be provided in the modular configuration discussed above where various sizes of the proximal body 26 can be interconnected to various sizes of distal stems 62 based on a particular size and/or configuration of a patient's anatomy. It should be appreciated, however, that femoral prosthesis 10 can be also be provided in a unitary configuration.

Figure 8:
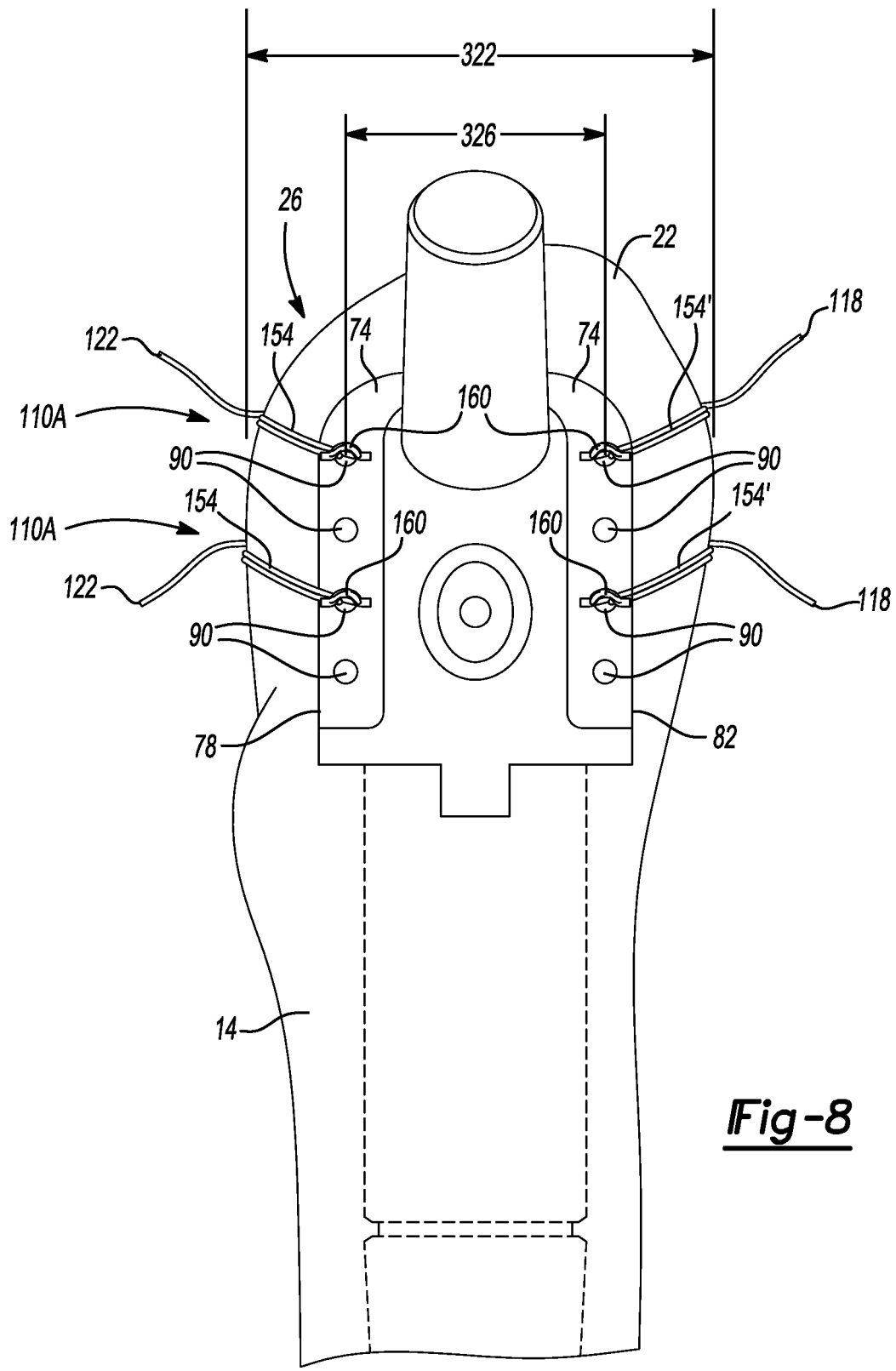

The trochanteric attachment region 34 can include a flanged region 74 on first and second sides 78, 82 of a proximal end 86 of the proximal body 26, as shown in FIGS. 1 and 2 with reference to FIG. 8. The flanged regions 74 can include a plurality of discrete attachment areas, such as apertures 90, configured to receive adjustable flexible member constructs for securing the separated greater trochanter 22, as will be discussed in greater detail below. It should be appreciated that while four apertures 90 are shown in the flanged regions 74, more or less apertures can be provided in proximal body 26 as may be desired for different applications and/or anatomical sizes. In this regard, and as will be discussed below, flanged regions 74 can also be provided with alternative attachment configurations, such as projections or tabs 104 (FIGS. 14 and 15) that can be provided in addition to or in lieu of apertures 90.

The proximal body 26 can be provided with a through hole 106 (FIG. 2) and a roughened or porous metal coating 108 to enhance biologic fixation and boney ingrowth, such as a layer of Regenerex® porous titanium construct or a layer of PPS® Porous Plasma Spray, available from Biomet Manufacturing Corp., having a place of business in Warsaw, Ind. In one exemplary configuration, components of the femoral prosthesis 10 can include those associated with the Mallory-Head Modular Calcar Revision System™ also available from Biomet Manufacturing Corp.

With additional reference to FIGS. 3-6, various adjustable flexible member constructs 110 are shown that can be associated with proximal body 26 for use in reattachment of greater trochanter 22. With particular reference to FIG. 3, a preformed adjustable self-locking flexible member construct 110A is provided according to the present teachings and can include a braided flexible member or suture 114 having a first end 118 and a second end 122. Flexible member 114 can include a body 126 that defines a longitudinal passage portion 130 therein between first and second ends 118, 122. The passage portion 130 can define a pair of apertures 134, 138 at opposed ends thereof.

To form construct 110A, the first end 118 can be passed through aperture 134 and passage portion 130 and out aperture 138 such that a portion 146 of flexible member 114 following first end 118 extends through passage portion 130. In a similar manner, second end 122 can be passed through aperture 138 and passage portion 130 and out aperture 134 such that a portion 150 of flexible member 114 following second end 122 also extends through passage portion 130. This configuration can form two loops 154 and 154', as shown in FIG. 3. It should be appreciated that while passage portion 130 is shown having two apertures or openings 134, 138, passage portion 130 can have additional openings and/or can include additional passage portions.

Figure 3A:
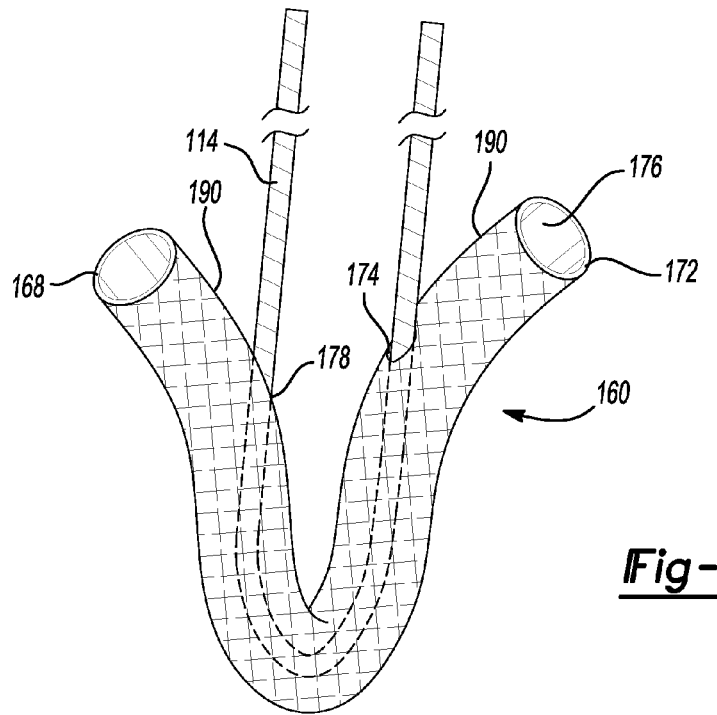

Adjustable flexible member construct 110A can include a pair of collapsible tubes or flexible anchors 160, as also shown in FIG. 3. One flexible anchor 160 can be coupled to loop 154 and the other flexible anchor 160 can be coupled to loop 154', as will be discussed below in greater detail. Flexible anchor 160 can be an elongate member having a sleeve or tubular configuration with first and second ends 168, 172 and an internal passage 176 extending therebetween, as shown in FIG. 3A. The flexible anchor 160 can be made of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials.

The flexible anchor 160 can have any properties that allow the flexible anchor 160 to change shape. In this regard, the flexible anchor 160 can be, for example, compliant, flexible, foldable, squashable, squeezable, deformable, limp, flaccid, elastic, low-modulus, soft, spongy or perforated, or have any other characteristic property that allows it to change shape. In some aspects, the flexible anchor 160 can be coated with biological or biocompatible coatings, and also can be soaked in platelets and other biologics, which can be easily absorbed by the flexible anchor 160. In one exemplary configuration, the flexible anchor 160 can be formed from a strand of No. 5 braided polyester suture. In other words, multiple fibers can be braided together to form a hollow braided flexible member having an internal passage.

As shown for example in FIG. 3A, flexible member 114 can be passed through a first opening 174 in a wall of the flexible anchor 160, guided into and along the internal passage 176, and passed out of the internal passage 176 through a second opening 178 in a wall of the flexible anchor 160 to associate flexible anchor 160 with loops 154, 154'. The openings 174, 178 can be positioned intermediately between the first and second ends 168, 172 of the flexible anchor 160 at a distance of, for example, one-quarter length from ends 168, 172. It will be appreciated that the openings 174, 178 can be apertures or voids in the woven fabric of the flexible anchor 160, such that the openings 174, 178 do not disrupt or break the weave of the flexible anchor 160 when made of braided or woven material. Further, portions of the flexible anchor 160 between the first and second ends 168, 172 and the corresponding first and second openings 174, 178, can define anchoring leg or tail portions 190 that can provide additional resistance for securing the flexible anchor 160 relative to a bone, fastener or implant, as will be discussed in greater detail herein. In one exemplary configuration, flexible member 114 can pass only through openings 174, 178 and a portion of the internal passage 176 extending therebetween to form a loop that does not extend through tail portions 190.

The pulling or tensioning of ends 118, 122 of flexible member construct 110A can cause reciprocal movement of portions 146, 150 relative to passage portion 130, and the loops 154, 154' can be reduced to a desired size and/or placed in a desired tension. Tension in loops 154, 154' can cause the body 126 defining the passage portion 130 to be placed in tension and therefore cause passage portion 130 to constrict about portions 146, 150 passed therethrough. This constriction reduces the diameter of passage portion 130, thus forming a mechanical interface between the exterior surfaces of portions 146, 150 and an interior surface of passage portion 130. This constriction results in static friction between the interior and exterior surfaces at the mechanical interface, causing the adjustable flexible member construct 110A to "automatically" lock in a reduced size or diameter configuration in which tension is maintained without use of a knot.

Figure 4A:
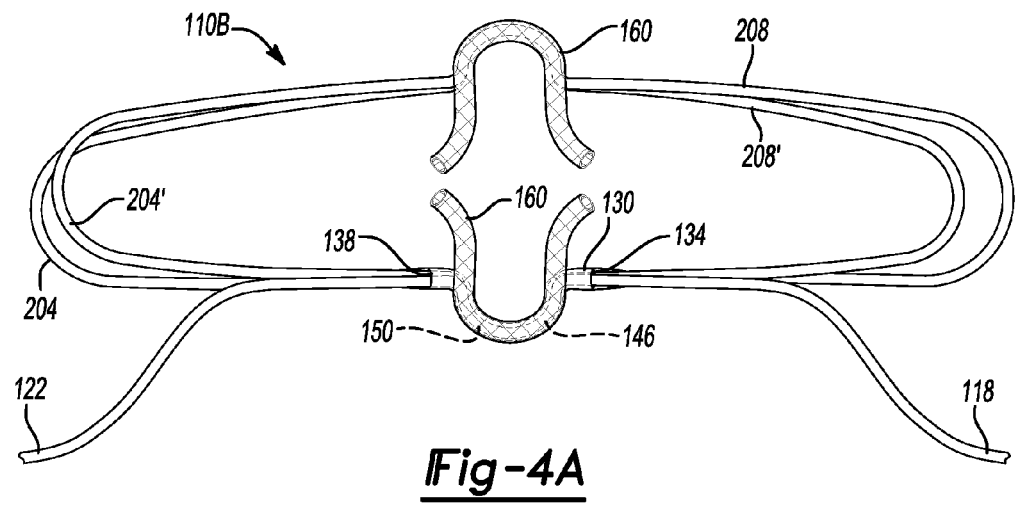
Figure 4B:
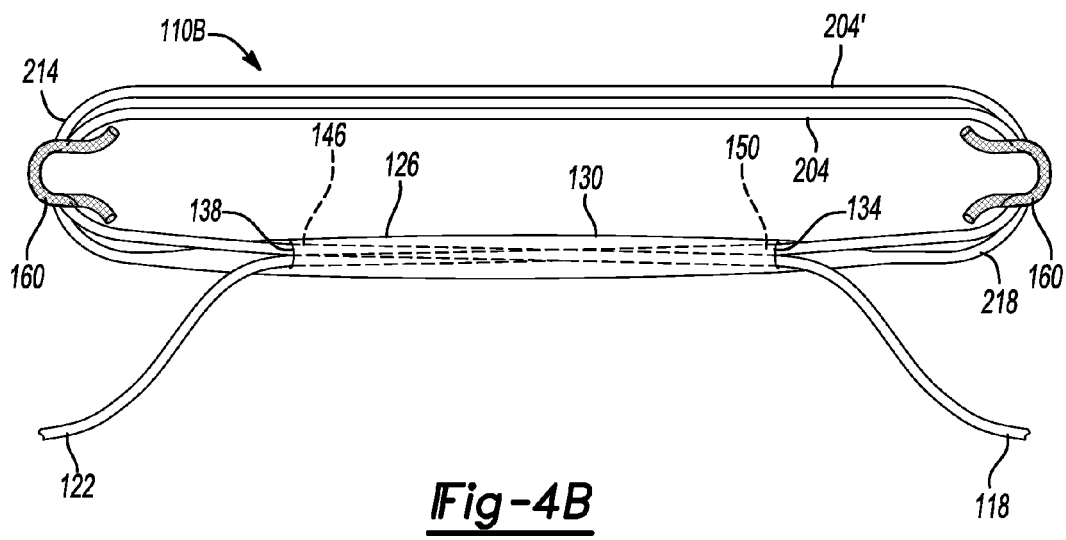

With reference to FIGS. 4A and 4B and continuing reference to FIGS. 3A and 3B, an alternative preformed adjustable self-locking flexible member construct 110B is shown. Construct 110B can be preformed to include a double loop configuration having two loops 204, 204' that each traverse a path from one end of passage portion 130 to the other end thereof, instead of each loop being disposed at respective opposite ends of passage portion 130 as in construct 110A. Flexible member construct 110B can be formed by passing the first end 118 of the flexible member through aperture 138, through passage portion 130 and out aperture 134. The second end 122 can be passed through aperture 134, through the passage portion 130 and out the aperture 138. In various aspects, the first and second apertures 134, 138 can be formed during the braiding process as loose portions between pairs of fibers defining the flexible member 114, as discussed above.

Passing ends 118, 122 through the apertures 134, 138 can form the loops 204, 204'. The loops 204, 204' can define mount or summit portions 208, 208' of the adjustable flexible member construct 110B and can be disposed generally opposite from the passage portion 130. Adjustable flexible member construct 110B can also include a pair of flexible anchors 160, as shown in FIGS. 4A and 4B. With reference to FIG. 4A, one flexible anchor 160 can be coupled to the summit portions 208, 208' of loops 204, 204' such that both loops 204, 204' extend through the respective flexible anchor 160 in a similar manner as discussed above with respect to flexible member construct 110A. The other flexible anchor 160 can be coupled to passage portion 130 such that passage portion 130 extends through the flexible anchor 160 in a similar manner as discussed above. With reference to FIG. 4B, adjustable flexible member construct 110B can alternatively include flexible anchors 160 coupled to loops 204, 204' at opposite sides 214, 218 of passage portion 130.

The longitudinal and parallel placement of the first and second ends 118 and 122 of the flexible member 114 within the passage portion 130 resists the reverse relative movement of the first and second portions 146, 150 of the flexible member construct 110B once it is tightened. The tensioning of the ends 118 and 122 can cause reciprocal movement of the portions 146, 150 relative to passage portion 130. Upon applying tension to the first and second ends 118 and 122, the loops 204, 204' can be reduced to a desired size or placed in a desired tension. Tension in the loops 204, 204' can cause the body 126 of the flexible member 114 defining the passage portion 130 to be placed in tension and therefore cause passage portion 130 to constrict about the portions 146, 150 similarly to the constriction discussed above with respect to construct 110A. This constriction can cause the adjustable flexible member construct 110B to "automatically" lock in a reduced size or smaller diameter configuration without the use of a knot.

Turning now to FIG. 5, an exemplary adjustable self-locking flexible member construct 110C is provided having only one loop 204. Adjustable flexible member construct 110C can be preformed in a similar manner as construct 110B, but with only one loop. Flexible member construct 110C can include a pair of flexible anchors 160 coupled thereto in a similar manner as discussed above with reference to FIGS. 4A and 4B.

With additional reference to FIG. 6, an adjustable flexible member construct 110D is provided according to various aspects of the present teachings. The adjustable flexible member construct 110D can be fashioned from flexible member 114 made of any biocompatible material including, but not limited to, non-resorbable polymers, such as polyethylene or polyester, resorbable polymers, and various combinations thereof. In various aspects, the adjustable flexible member construct 110D can include a hollow material or core to allow for appropriate tensioning, as will be discussed herein. In various aspects, the flexible member 114 can be hollow or a braided or a multiple-filament braided suture structure having a hollow core. In various aspects, the suture can be resorbable.

The adjustable flexible member construct 110D can include a first end 220, a first formed passage portion 224, a second end 228, a second formed passage portion 232, and a fixed length loop portion 236 connecting the first and second passage portions 224, 232, as shown in FIG. 6. In one exemplary aspect, flexible member construct 110D can include an elongated body 240 having an exterior surface and an interior surface defining an elongated passage between the first and second ends 220, 228. The body 240 can define the first and second passage portions 224, 232 and the fixed length portion 236 therebetween. Passage portions 224, 232 can each include first apertures 244, 248 positioned proximate one end 252 thereof, and second apertures 256, 260 positioned proximate a second opposite end 264 thereof. The passage portions 224, 232 can be formed to have a larger width or diameter than remaining portions of flexible member 114, as shown for example in FIG. 6. Alternatively, the passage portions 224, 232 can be formed initially to have the same width or diameter as the remaining portions of flexible member 114, later expanding in diameter during the construction process. In various aspects, the first and second apertures 244, 248, 256, 260 can be formed during a braiding process of flexible member 114 as loose portions between pairs of fibers defining flexible member 114, or can be formed during the construction process. Alternatively, the first and second ends 220, 228 can be pushed between individual fibers of the braided flexible member 114.

To form the adjustable flexible member construct 110D, first end 220 can be passed through second passage portion 232 via first and second apertures 248, 260, as generally shown in FIG. 6. In a similar manner, second end 228 can be passed through the first passage portion 224 via the first and second apertures 244, 256, as also shown in FIG. 6. Subsequently, first end 220 can be passed through the first passage portion 224 via second and first apertures 256 and 244, respectively. First end 220 can follow a path that is opposite in direction to a path followed by a portion 272 of the flexible member 114 that has already passed through first passage portion 224 while following second end 228 through first and second apertures 244 and 256. Similarly, second end 228 can be passed through the second passage portion 232 via second and first apertures 260 and 248, respectively. Second end 228 can follow a path that is opposite in direction to a path followed by a portion 276 of the flexible member 114 that has already passed through second passage portion 232 while following first end 220 through first and second apertures 248 and 260. This results in portions 280, 284 of flexible member 114 being positioned parallel or substantially parallel to portions 272, 276 in passage portions 224, 232. Passing the first and second ends 220, 228 though passage portions 224, 232 as discussed above forms adjustable loops 288, 292, as shown in FIG. 6. The first and second ends can be passed through the same apertures in each passage portion 224, 232 or, alternatively, through separate apertures in each passage portion 224, 232.

The adjustable flexible member construct 110D can provide a double adjustable loop configuration via adjustable loops 288, 292 while also providing portion 236, which can have a fixed length between the passage portions 224, 232. This configuration can be used, for example, to couple a flexible anchor 160 to loops 288, 292 and couple fixed length portion 236 to flexible anchor 160 and/or another device.

Flexible member constructs 110A-110D also can be provided with an antibiotic and/or platelet concentrate coating to resist bacterial adhesion and/or promote healing. In this regard, flexible member constructs 110A-110D, can be preconfigured with such a coating or the coating can be applied intraoperatively. Further, the surgeon can also apply the platelet coating to the fractured or resected area of the greater trochanter 22 during the trochanteric reattachment procedure.

With additional reference to FIGS. 7-16, the use of flexible member constructs 110A-110D in various exemplary trochanteric reattachment configurations and procedures will now be discussed. With initial reference to FIG. 7, proximal femoral prosthesis 10 is shown implanted in femur 14. A proximal portion of femur 14 has been resected and the greater trochanter 22 has been separated, as discussed above and shown in FIG. 7 with reference to exemplary line 300. The greater trochanter 22 has been separated along exemplary line 300, during a hip reconstruction procedure for example, and is shown repositioned or relocated against femur 14 along line 300 and against the trochanteric engaging region 30 of proximal body 26. Flexible member constructs 110A-110D individually, or in various combinations with each other and/or additional fixation devices, can be used to compress and secure the greater trochanter 22 to femur 14 and proximal body 26 to assist healing, as will be discussed below. While the following discussion continues with reference to greater trochanter 22 of femur 14, it should be appreciated that the techniques can also be applied to the greater trochanter of the humerus in configurations similar to those shown in FIGS. 7-16.

With particular reference to FIGS. 7 and 8, a pair of adjustable flexible member constructs 110A are shown coupled to proximal body 26 to compress and secure greater trochanter 22 to femur 14 and proximal body 26. In the exemplary configuration illustrated, the flexible anchor 160 coupled to loop 154 of construct 110A can be positioned through aperture 90 of flanged region 74 on first side 78 from a lateral side 310 to a medial side 314. Flexible member construct 110A can then be wrapped around an outer surface 318 of greater trochanter 22 and flexible anchor 160 coupled to loop 154' can be positioned though aperture 90 on second side 82, as shown in FIG. 7 with reference to FIG. 8. As also shown, more than one flexible member construct 110A can be used, as may be desired depending on particular aspects of the anatomy and/or procedure being performed.

In this configuration, flexible member constructs 110A extend around outer surface 318 without extending through greater trochanter 22 to reach apertures 90. In this regard, depending on a width 322 of the greater trochanter 22 relative to a width 326 between a corresponding pair of apertures 90, the flexible anchors 160 may need to be positioned through apertures 90 before the greater trochanter 22 is relocated against trochanteric engaging region 30 because the greater trochanter 22 can cover access to apertures 90. For example, and with particular reference to FIG. 8, greater trochanter 22 is shown as having a width 322 wider than the width 326 between apertures 90 such that greater trochanter 22 can cover apertures 90 upon being relocated against proximal femoral body 26.

The flexible member constructs 110A can be coupled to any of the apertures 90 in the flanged regions 74 in various patterns and configurations, as may be required depending on a patient's greater trochanter geometry, as will be discussed below. In addition, various other flexible member constructs 110B-110D can be used in addition to and/or in lieu of constructs 110A to secure the greater trochanter 22, as will also be discussed below.

Figure 9:
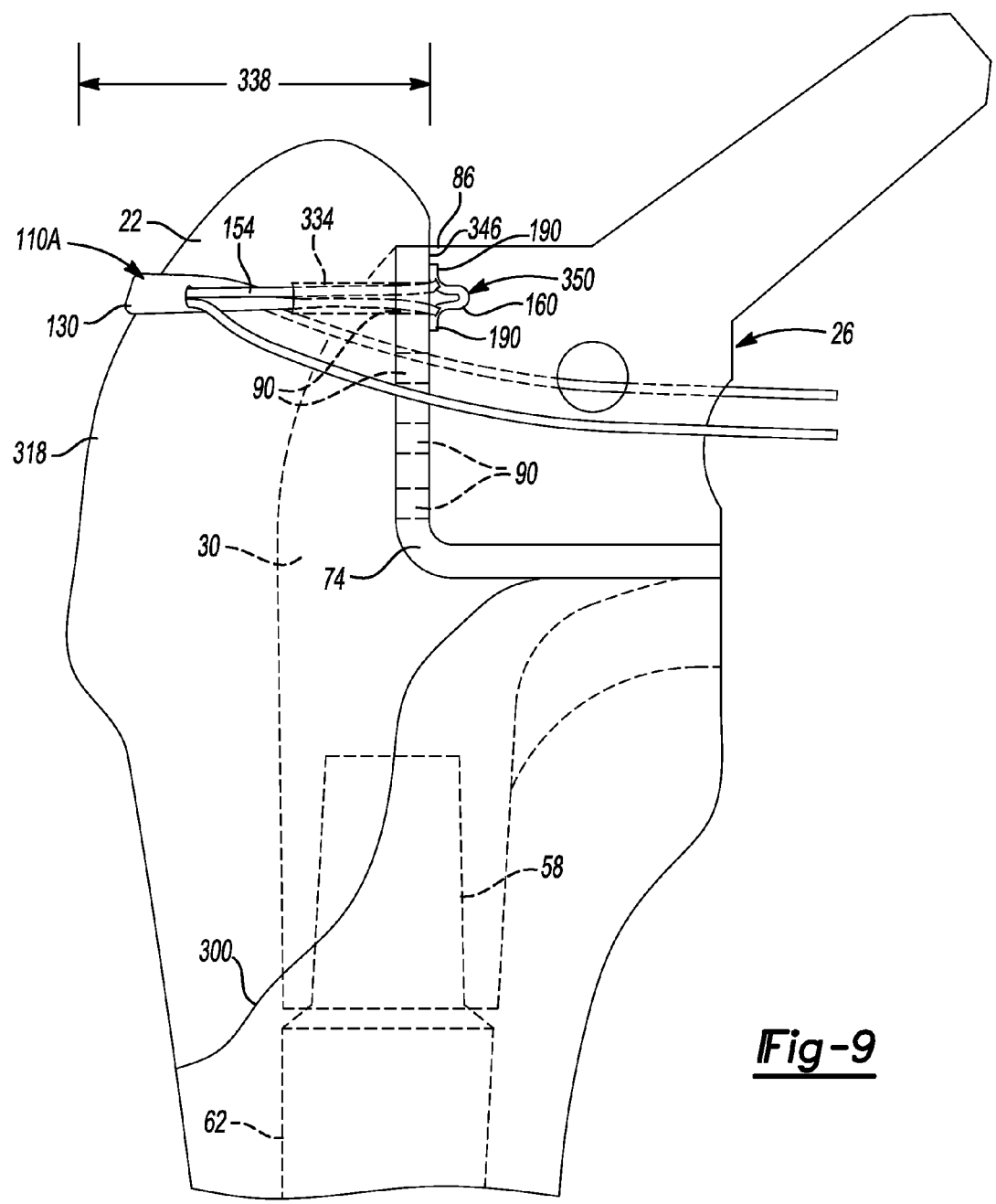

With additional reference to FIG. 9, a bore 334 can be formed through the greater trochanter 22 in alignment with an aperture 90 selected to receive one of the adjustable flexible member constructs 110. In the exemplary configuration illustrated, construct 110A is shown extending through bore 334 and through aperture 90. Depending on the angle of approach chosen to align bore 334 with aperture 90, as well as the form of outer surface 318, bore 334 can extend through a portion or all of a thickness 338 of greater trochanter 22. For example, bore 334 shown in FIG. 9 extends through a portion of the thickness 338 of greater trochanter 22. In one exemplary aspect, bores 334 can be used when the greater trochanter 22 remains partially attached to the femur 14 and access to apertures 90 can be limited. While FIG. 9 illustrates use of one flexible member construct 110A, it should be appreciated that multiple flexible member constructs 110A-110D can be used with or without bores 334 having varying lengths relative to thickness 338 of greater trochanter 22.

In the configurations illustrated in FIGS. 7-9, the free ends 118, 122 of each flexible member construct 110A coupled to proximal body 26 can then be tensioned to reduce a size of loops 154, 154' and compress the greater trochanter 22 into a secured engagement with femur 14 and proximal body 26. The tail portions 190 of anchors 160 can engage a surface 346 of the flanged regions 74 adjacent the apertures to anchor the loops 154, 154' relative to the proximal body 26, as shown in FIGS. 7-9. In one exemplary configuration, tail portions 190 as well as the entire anchor 160, can bunch together, collapse, expand and/or change shape to a second shape, configuration or locking profile 350 to secure loops 154, 154' to flanged regions 74. It should be appreciated that flexible anchors 160, upon being anchored to an appropriate surface, such as surface 346 associated with apertures 90, permit the associated flexible member loop to slide relative to the flexible anchor such that the loops can be reduced in size upon being tensioned. Flexible construct 110A can automatically lock under tension, as discussed above, after which a portion of ends 118, 122 can be trimmed and removed. This configuration can compress the greater trochanter 22 along line 300 with minimal modification to the greater trochanter 22, as compared to other procedures or techniques using a trochanter bolt extending through greater trochanter 22.

Figure 10:
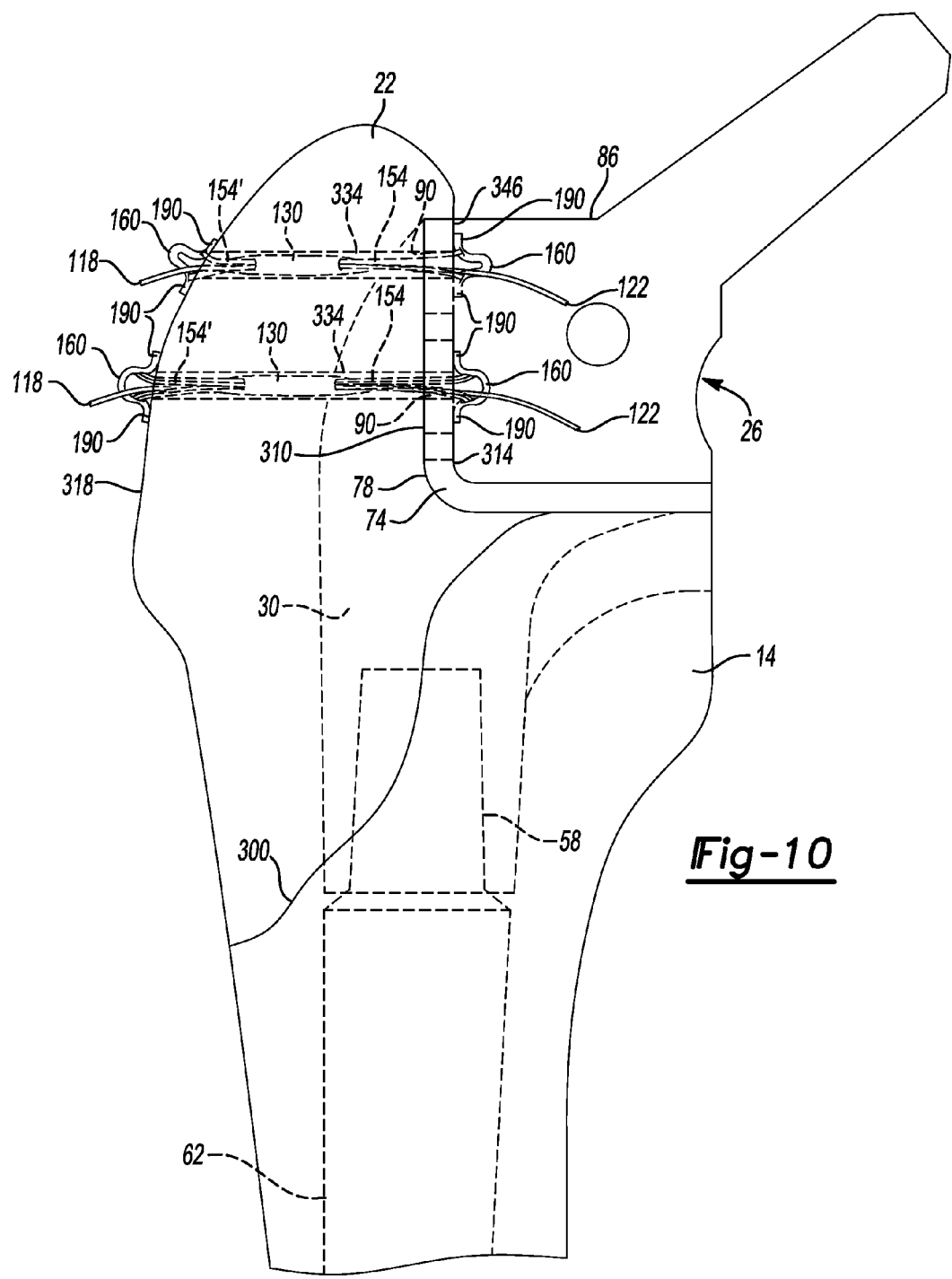

With additional reference to FIG. 10, another exemplary technique for securing the greater trochanter 22 is shown in accordance with the present teachings. In this exemplary configuration, a bore 334 can extend through a partial thickness of the greater trochanter 22 (FIG. 9) or through an entire thickness, as shown in FIG. 10. Bore 334 can be formed in greater trochanter 22 relative to the apertures 90 selected for use with one of the adjustable flexible constructs 110A-110D. In this regard, it should be appreciated that while bore 334 is shown in FIG. 10 relative to the first side 78 of proximal body 26, a corresponding bore 334 can formed in greater trochanter 22 relative to the corresponding aperture 90 on the second side 82 (FIG. 8) of proximal body 26. In one exemplary configuration, the pair of bores 334 and adjustable flexible member constructs shown in FIG. 10 relative to the first side 78 of proximal body 26 can be reproduced as a mirror image relative to the second side 82 of proximal body 26. As a result, the following discussion will continue with reference to the first side 78, but will be understood to apply to the second side 82 as well, unless otherwise indicated.

Once bores 334 are formed in greater trochanter 22 to align with the selected apertures 90, one of the adjustable flexible member constructs 110A-110D, such as construct 110A shown in FIG. 10, can be used to secure greater trochanter 22 to proximal body 26 via apertures 90. In the exemplary configuration illustrated, flexible anchor 160 coupled to loop 154 can be positioned through each bore 334 and corresponding aperture 90 in flanged region 74. Once flexible anchor 160 is positioned through aperture 90, the tail portions 190 can engage surface 346 adjacent aperture 90 to secure loop 154 relative to proximal body 26 in a similar manner as discussed above. Free end 122 of each construct 110A can also extend through apertures 90 while the opposite free end 118 as well as loop 154' can extend from the greater trochanter 22 relative to an opening 354 of bore 334 opposite flanged region 74, as also shown in FIG. 10.

The free ends 118, 122 of flexible member construct 110A can be tensioned to reduce a size of the loops 154, 154' in a manner similar to that discussed above. Tensioning the free ends 118, 122 and reducing a size of loops 154, 154' can seat each flexible anchor 160 relative to the outer surface 318 and surface 346 of proximal body 26 and draw the greater trochanter 22 into secured engagement with proximal body 26 and femur 14, as shown in FIG. 10. It should be appreciated that while FIG. 10 illustrates use of flexible member construct 110A, any of flexible member constructs 110A-110D can be used alone or in various combinations with each other. In this regard, it should also be appreciated that different flexible member constructs could be used on the first and second sides 78, 82 of proximal body 26, as may be desired.

Figure 11:
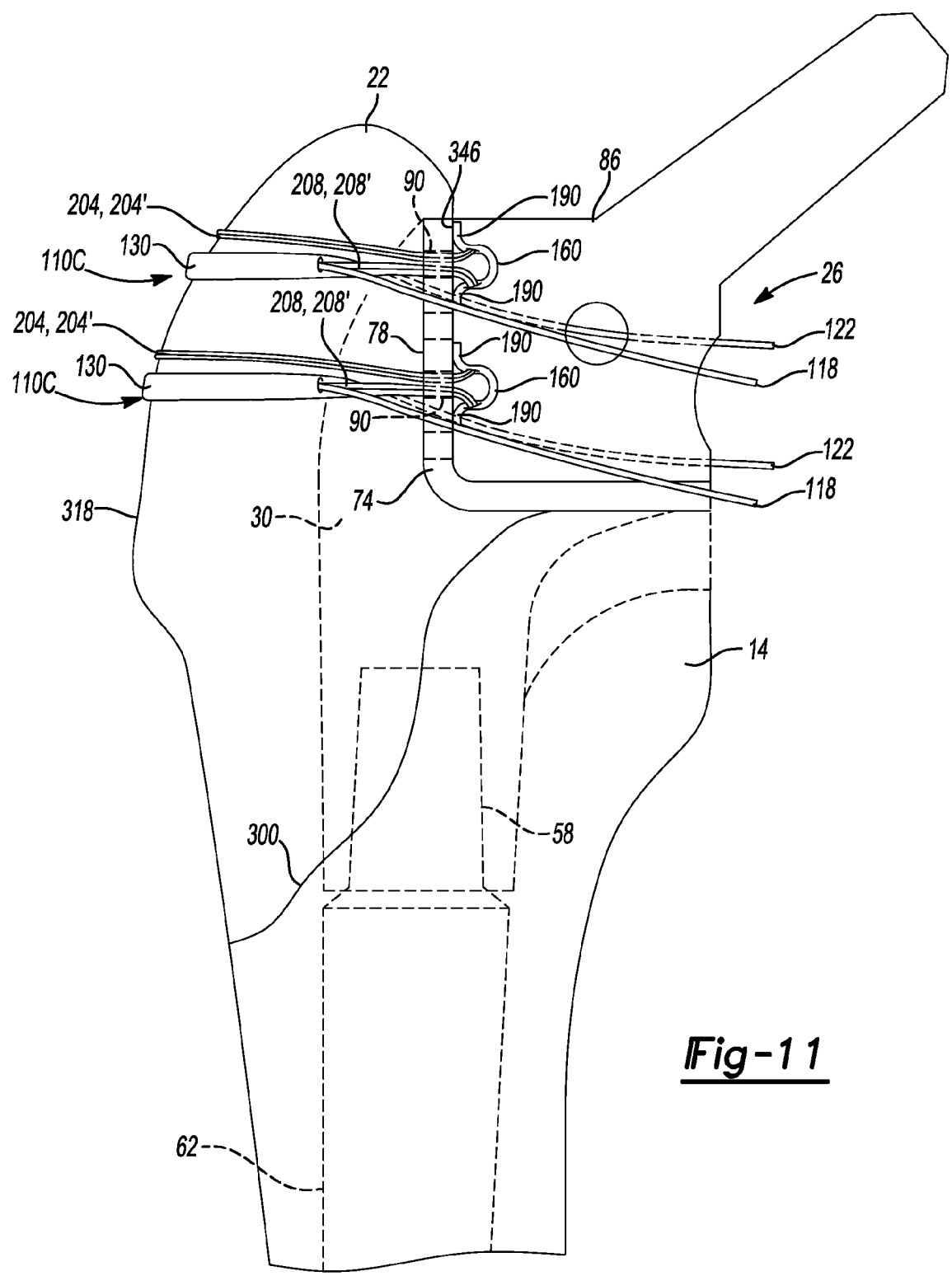
Figure 12:
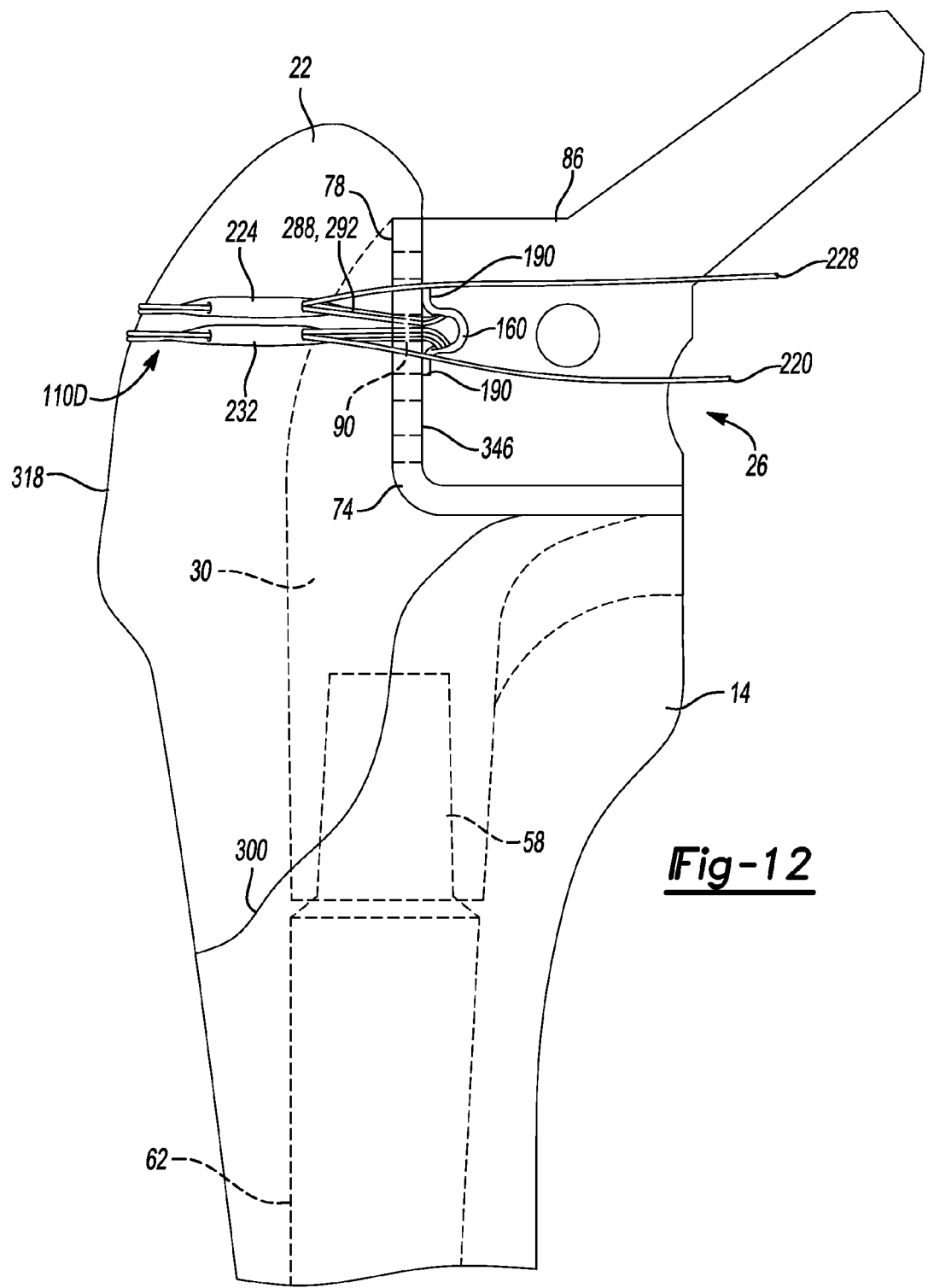

With additional reference to FIGS. 11 and 12, and reference back to FIG. 8, adjustable flexible member constructs 110B and 110D are shown coupled to proximal body 26 to compress and secure greater trochanter 22 to femur 14 and proximal body 26. With particular reference to FIG. 11, flexible member constructs 110B are shown coupled to apertures 90 and wrapping around outer surface 318 of greater trochanter 22 in a similar manner as discussed above with reference to FIG. 7 and flexible member construct 110A. In this illustrated configuration, free ends 118, 122 can extend about the first and second sides of proximal body 26 as the passage portion 130 and loops 204, 204' of flexible member construct 110B can extend around or relative to outer surface 318 of greater trochanter 22.

In an alternative configuration where flexible anchors 160 are coupled to the passage portion 130 and summit portions 208, 208', as shown in FIG. 4A, the passage portion 130 can be coupled to apertures 90, say on the first side 78, and the summit portions can then be coupled to apertures 90 on the second side 82. In this configuration, the free ends 118, 122 can extend from the respective apertures 90 relative to one side of the proximal body 26 instead of relative to both the first and second sides 78, 82. In either configuration, the free ends 118, 122 can be tensioned in the manner discussed above to draw greater trochanter 22 into tight engagement with proximal body 26 and femur 14 to secure greater trochanter 22 thereto and promote healing.

As can be seen in FIG. 12 with reference back to FIGS. 6 and 8, flexible member construct 110D is shown coupled to proximal body 26 and securing greater trochanter 22 thereto and to femur 14. In this configuration, one of the flexible anchors 160, such as flexible anchor 160 coupled to loops 288, 292 can be positioned through aperture 90 on first side 78 and the other flexible anchor 160 coupled to fixed portion 236 can be positioned through aperture 90 on second side 82. The free ends 220, 228 can extend about a side of proximal body 26, such as the first side 78 shown in FIG. 11, that includes the passage portions 224, 232 positioned relative thereto. The free ends 220, 228 can be tensioned to reduce a size of loops 288, 292 and draw greater trochanter 22 into compressed engagement with proximal body 26 and femur 14 to secure greater trochanter 22 relative thereto and promote healing. In a similar manner to the other configurations discussed above, more than one flexible member construct 110D can be used and secured relative to apertures 90 as may be required or desired by the physician.

Figure 13:
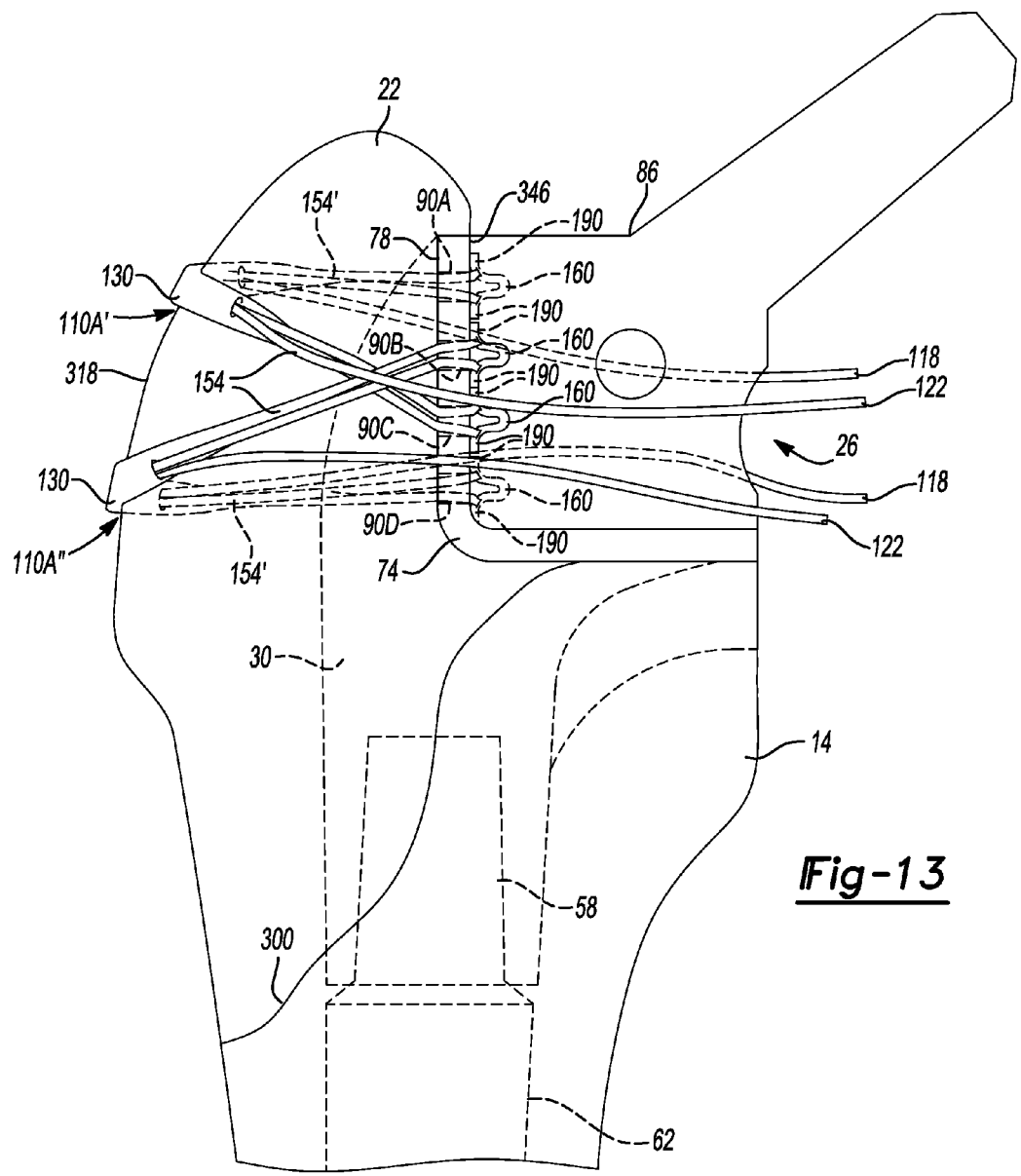

With additional reference to FIG. 13 and reference back to FIG. 8, a pair of flexible member constructs 110A are shown coupled to proximal body 26 and securing greater trochanter 22 relative thereto and to femur 14 in accordance with the present teachings. In this configuration, the flexible member constructs 110A can be secured to apertures 90 in different positions between the first and second sides 78, 82 of proximal body 26 such that the second side 82 is not a mirror image of the first side 78. For ease of discussion, the flexible member constructs 110 in this configuration will be referred to as constructs 110A' and 110A". In this exemplary configuration, the loop 154 of construct 110A' can be coupled to a third aperture 90C relative to the proximal end 86 of flanged region 74 on first side 78, as shown in FIG. 13. Flexible member construct 110A' can extend around outer surface 318 of greater trochanter 22 and loop 154' can be coupled to a first aperture 90A relative to proximal end 86. In this configuration, flexible member construct 110A' can extend around greater trochanter 22 at an angle due to being positioned in first and third apertures 90A, 90C that are positioned at different distances relative to proximal end 86.

In a similar manner, flexible member construct 110A" can be coupled to proximal body 26 such that loop 154 is coupled to a second aperture 90B on first side 78 and loop 154' can be coupled to a fourth aperture 90D on second side 82. Flexible member construct 110A" can extend around outer surface of greater trochanter 22 such that a portion of flexible construct 110A" overlaps a portion of flexible construct 110A' to provide additional retention and securement of greater trochanter 22 to proximal body 26 and femur 14, as shown in FIG. 13. In the exemplary configuration illustrated, flexible constructs 110A' and 110A" overlap each other in a crisscross manner to form an X-shaped pattern. It should be appreciated that while FIG. 13 illustrates use of two flexible member constructs 110A, other flexible member constructs can be used in various combinations to overlap each other in the manner discussed above.

Figure 14:
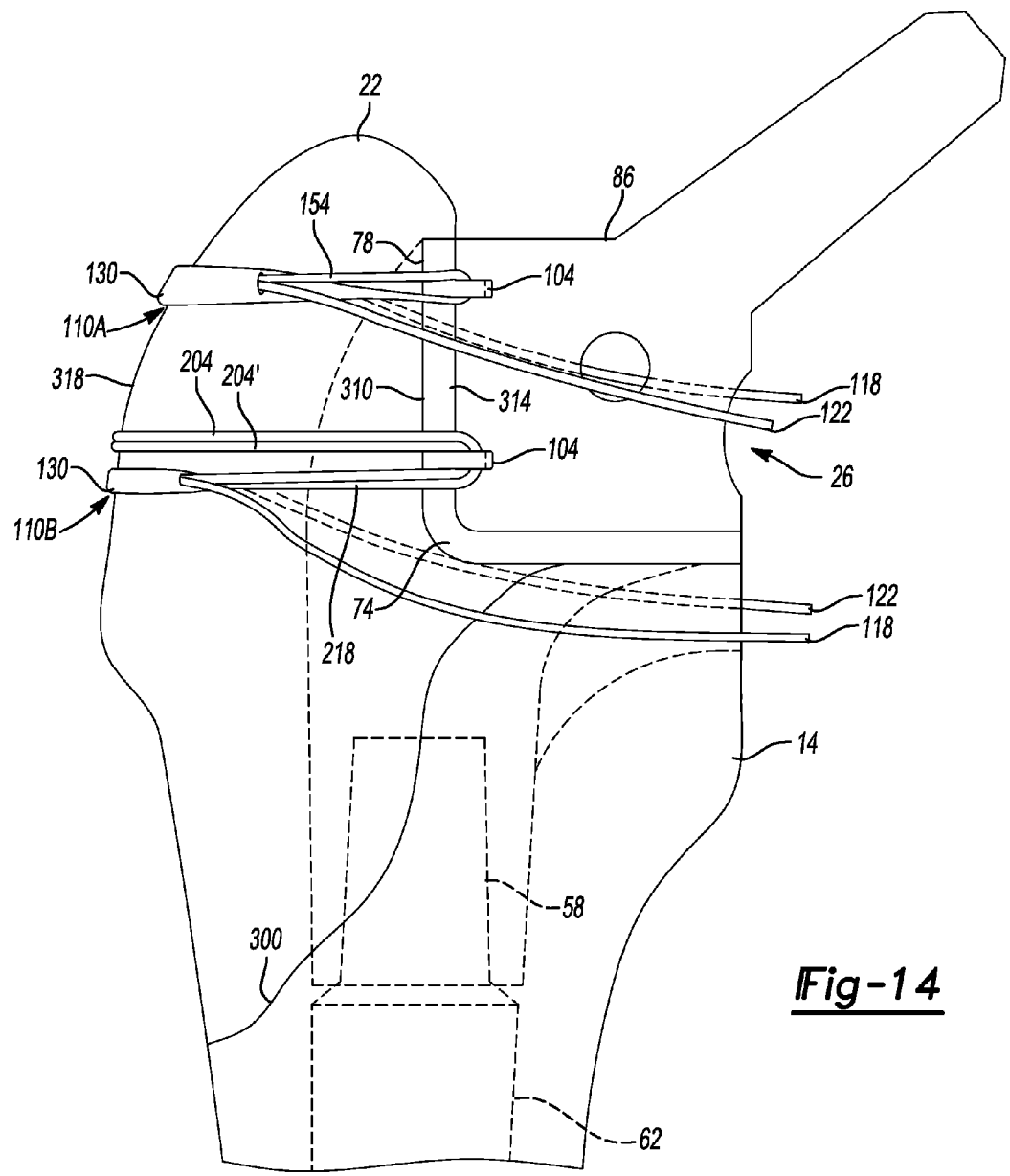
Figure 15:
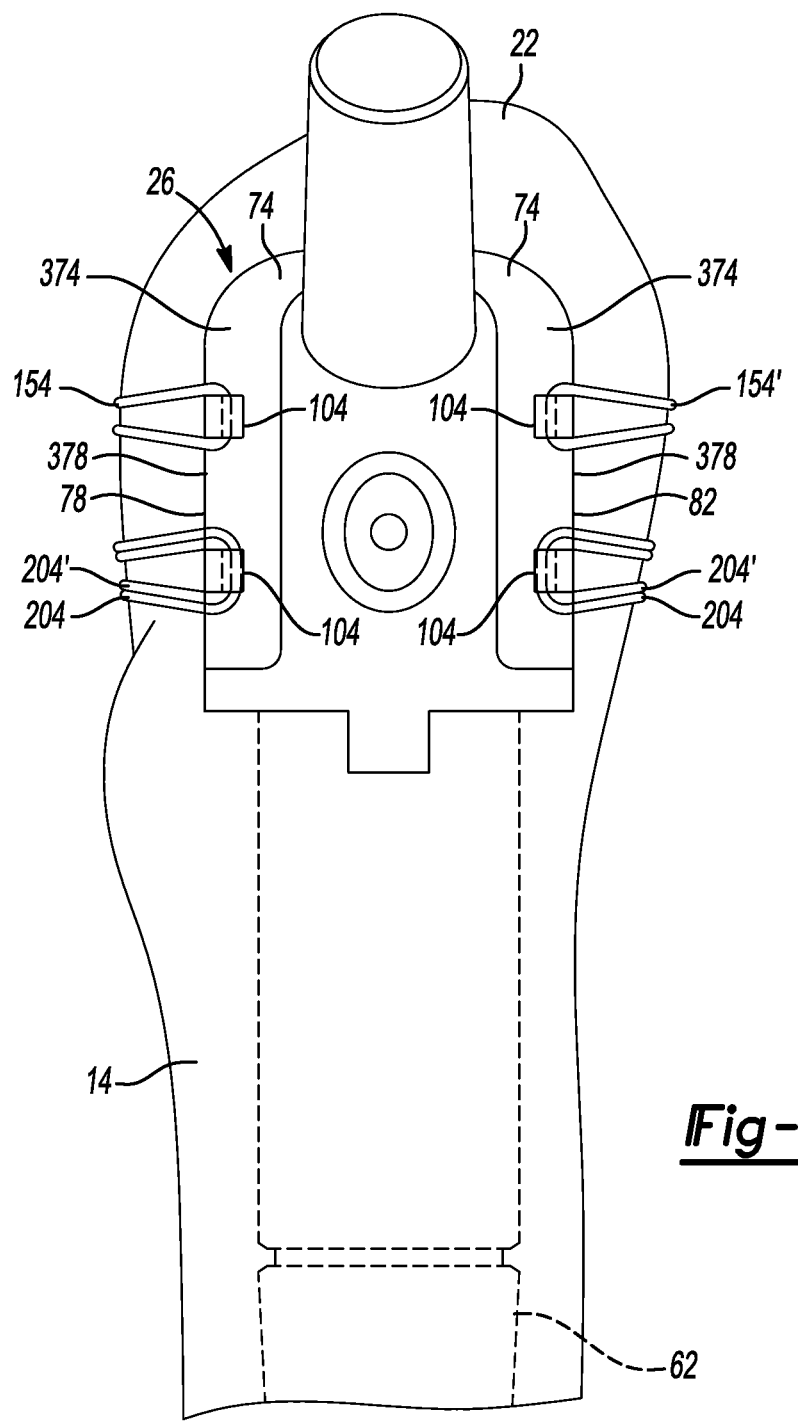

Turning now to FIGS. 14 and 15 with reference back to FIGS. 3 and 4B, another exemplary configuration is shown for reattachment of greater trochanter 22 in accordance with the present teachings. In this configuration, proximal body 26 can include the plurality of projections or tabs 104 configured to removably receive a loop of one of flexible member constructs 110A-110D. The tabs 104 can be provided in addition to or in lieu of apertures 90. In one exemplary configuration, the tabs 104 can extend from a surface 374 inboard from a perimeter edge 378 of the first and second sides 78, 82 of the flanged regions 74, as shown in FIG. 15. It should be appreciated that while a pair of tabs 104 is shown in FIGS. 14 and 15 associated with first and second sides 78, 82, more or less tabs 104 can be provided on proximal body 26, as may be required.

In this configuration, the loops of adjustable flexible member constructs 110A-110D can be removably positioned over the tabs 104 to couple the loops to proximal body 26. In this regard, the flexible anchors 160 are not necessary for use in coupling the flexible member constructs to proximal body 26. However, it should be appreciated that the flexible member constructs 110A-110D can be used with tabs 104 while also carrying the flexible anchors 160.

In the exemplary configuration illustrated, loop 154 of flexible member construct 110A can be coupled to tab 104 on first side 78 and loop 154' can be coupled to tab 104 on second side 82 such that flexible member construct 110A extends around outer surface 318 of greater trochanter 22, as shown in FIGS. 14 and 15. Similarly, adjustable flexible member construct 110B is shown have loops 204, 204' on side 218 of passage portion 130 coupled to tab 104 on first side 78 and loops 204, 204' on side 214 of passage portion 130 coupled to tab 104 on second side 82 of proximal body 26. The free ends 118, 122 of flexible member constructs 110A, 110B can be tensioned to reduce a size of the respective loops and draw greater trochanter 22 into secure engagement with proximal body 26 and femur 14 in a similar manner as discussed above. Again, it should be appreciated that other flexible member constructs can be used in addition to, in lieu of, or in combination with constructs 110A and 110B and tabs 104 of proximal body 26. It should also be appreciated that proximal body 26 with tabs 104 can be used with the various techniques and configurations discussed herein in place of apertures 90 or in combination with apertures 90 to facilitate securing greater trochanter 22 to proximal body 26 and femur 14 to promote healing.

Figure 16:
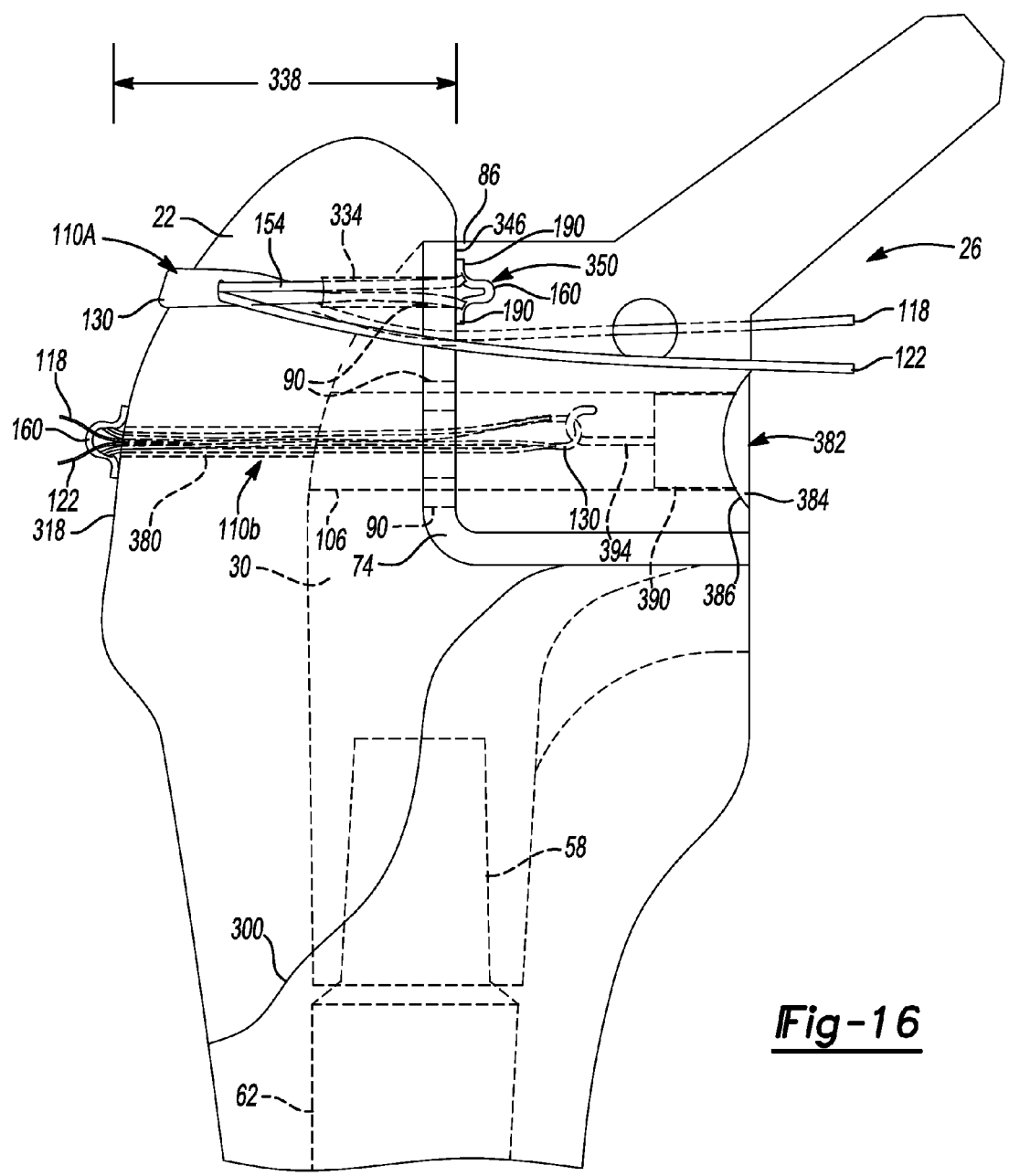

Turning now to FIG. 16 and with reference back to FIG. 4A, another exemplary configuration is shown for reattachment of greater trochanter 22 in accordance with the present teachings. In this configuration, an attachment device can be used in connection with the through bore 106 of proximal body 26 to secure the greater trochanter 22 to femur 14 and proximal body 26. In one exemplary configuration, the attachment member can include a medial plug 382 having a head 384 with an angled bone engaging surface 386 and a body portion 390 extending therefrom. An attachment member, such as hook 394, can extend from an end of the body portion 390 opposite the head 284, as shown in FIG. 16. In one exemplary configuration, the head 384 can include a larger diameter than a diameter of through bore 106, as also shown in FIG. 16. It should be appreciated that the medial plug 382 can include various attachment members configured to receive one of the flexible member constructs 110A-110D and can be provided with or without the head 384 having the angled bone engaging surface 386.

A bore 380 can be formed through greater trochanter 22 in alignment with the through bore 106 of proximal body 26. A flexible member construct, such as construct 110B, can be coupled to the hook 394 at one end and can be secured to outer surface 318 of greater trochanter 22 at an opposite end, as shown in FIG. 16. In one exemplary configuration, the flexible construct 110B of FIG. 4A can include one of the flexible anchors 160 coupled to the summit regions 208, 208', while the other flexible anchor 160 coupled to passage portion 130 is not required. With this construct, the passage portion 130 can be passed through bores 380 and 106 and coupled to the hook member 394. The flexible anchor 160 can be positioned relative to outer surface 318 and the free ends 118, 122 can be tensioned to secure greater trochanter 22 relative to proximal body 26 and femur 14, as also shown in FIG. 16.

It should be appreciated that bore 380 can be formed at various angles through greater trochanter 22 relative to bore 26, and that a plurality of bores 380 can be formed for receiving a corresponding plurality of flexible member constructs. In addition, it should be appreciated that the greater trochanter 22 can be secured using medial plug 382 as discussed above along with various other techniques and flexible member constructs 110A-110D, including those discussed above in connection with FIGS. 7-15.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A method for trochanteric reattachment, comprising:
positioning a femoral prosthesis relative to a proximal portion of a femur;
coupling a first portion of a self-locking adjustable flexible member construct to a first attachment region of the femoral prosthesis;
coupling a second portion of the self-locking adjustable flexible member construct to a second attachment region of the femoral prosthesis, the second portion being opposite the first portion;
positioning a trochanter relative to the femur and a trochanteric engaging region of the femoral prosthesis;
positioning the self-locking adjustable flexible member construct around an outer surface of the trochanter; and
tensioning free ends of the self-locking adjustable flexible member construct to draw the trochanter into secure engagement with the femoral prosthesis and the femur via the self-locking adjustable flexible member construct in an absence of a knot;
positioning at least one of the plurality of separate self-locking adjustable flexible member constructs around the outer surface of the trochanter in an overlapping manner with another one of the plurality of separate elf-locking adjustable flexible member constructs so as to form an X-shaped pattern.

2. The method of claim 1, wherein coupling the first portion of the self-locking adjustable flexible member construct to the first attachment region includes coupling the first portion of a plurality of separate self-locking adjustable flexible member constructs to discrete attachment areas of the first attachment region of the femoral prosthesis; and
wherein coupling the second portion of the self-locking adjustable flexible member construct to the second attachment region includes coupling the second portion of the plurality of separate self-locking adjustable flexible member constructs to discrete attachment areas of the second attachment region of the femoral prosthesis.

3. A method for trochanteric reattachment, comprising:
positioning a femoral prosthesis relative to a proximal portion of a femur;
coupling a first portion of a self-locking adjustable flexible member construct to a first attachment region of the femoral prosthesis;
coupling a second portion of the self-locking adjustable flexible member construct to a second attachment region of the femoral prosthesis, the second portion being opposite the first portion;
positioning a trochanter relative to the femur and a trochanteric engaging region of the femoral prosthesis;
positioning the self-locking adjustable flexible member construct around an outer surface of the trochanter; and
tensioning free ends of the self-locking adjustable flexible member construct to draw the trochanter into secure engagement with the femoral prosthesis and the femur via the self-locking adjustable flexible member construct in an absence of a knot;
wherein coupling the first portion of the self-locking adjustable flexible member construct to the first attachment region includes coupling a first adjustable loop of the self-locking adjustable flexible member construct to the first attachment region of the femoral prosthesis; and
wherein coupling the second portion of the self-locking adjustable flexible member construct to the second attachment region includes coupling a second adjustable loop of the self-locking adjustable flexible member construct to the second attachment region of the femoral prosthesis.

4. The method of claim 3, wherein coupling the first adjustable loop of the self-locking adjustable flexible member construct to the first attachment region includes positioning a first flexible anchor slidably coupled to the first adjustable loop through a first aperture defined by the first attachment region and retaining the first flexible anchor relative to the first attachment region; and
wherein coupling the second adjustable loop of the self-locking adjustable flexible member construct to the second attachment region includes positioning a second flexible anchor slidably coupled to the second adjustable loop through a second aperture defined by the second attachment region and retaining the second flexible anchor relative to the second attachment region.

5. The method of claim 3, wherein coupling the first adjustable loop of the self-locking adjustable flexible member construct, to the first attachment region includes positioning the first adjustable loop over a tab extending from the first attachment region of the femoral prosthesis and retaining the first adjustable loop relative to the first attachment region; and
wherein coupling the second adjustable loop of the self-locking adjustable flexible member construct to the second attachment region includes positioning the second adjustable loop over a tab extending from the second attachment region of the femoral prosthesis and retaining the second adjustable loop relative to the second attachment region.

6. The method of claim 3, further comprising:
forming a first bore through a portion of the trochanter so as to align with the first attachment region of the femoral prosthesis;
passing the first portion of the self-locking adjustable flexible member construct through the first bore;
forming a second bore through another portion of the trochanter so as to align with the second attachment region of the femoral prosthesis; and passing the second portion of the self-locking adjustable flexible member construct through the second bore.

7. A method for trochanteric reattachment, comprising:
positioning a femoral prosthesis relative to a proximal portion of a femur;
coupling a first portion of a self-locking adjustable flexible member construct to a first attachment region of the femoral prosthesis;
coupling a second portion of the self-locking adjustable flexible member construct to a second attachment region of the femoral prosthesis, the second portion being opposite the first portion;
positioning a trochanter relative to the femur and a trochanteric engaging region of the femoral prosthesis;
positioning the self-locking adjustable flexible member construct around an outer surface of the trochanter; and
tensioning free ends of the self-locking adjustable flexible member construct to draw the trochanter into secure engagement with the femoral prosthesis and the femur via the self-locking adjustable flexible member construct in an absence of a knot;
wherein coupling the first portion of the self-locking adjustable flexible member construct to the first attachment region of the femoral prosthesis includes coupling the first portion of a pair of adjustable loops of the self-locking adjustable flexible member construct to a discrete attachment area of the first attachment region of the femoral prosthesis; and
wherein coupling the second portion of the self-locking adjustable flexible member construct to the second attachment region of the femoral prosthesis includes coupling the second portion of the pair of adjustable loops to a discrete attachment area of the second attachment region of the femoral prosthesis.

8. The method of claim 7, wherein coupling the first portion of the pair of adjustable loops of the self-locking adjustable flexible member construct to the discrete attachment area of the first attachment region includes coupling a first flexible anchor slidably coupled to the pair of adjustable lobos through a first aperture of the first attachment region and retaining the pair of adjustable loops relative to the first aperture; and
wherein coupling the second portion of the pair of adjustable loops to the discrete attachment area of the second attachment region includes coupling a second flexible anchor slidably coupled to the pair of adjustable loops through a second aperture of the second attachment region and retaining the pair of adjustable loops relative to the second aperture.

9. A method for trochanteric reattachment, comprising:
positioning a femoral prosthesis relative to a proximal portion of a femur;
coupling a first portion of a self-locking adjustable flexible member construct to a first attachment region of the femoral prosthesis;
coupling a second portion of the elf-locking adjustable flexible member construct to a second attachment region of the femoral prosthesis, the second portion being opposite the first portion;
positioning a trochanter relative to the femur and a trochanteric engaging region of the femoral prosthesis;
positioning the self-locking adjustable flexible member construct around an outer surface of the trochanter; and
tensioning free ends of the self-locking adjustable flexible member construct to draw the trochanter into secure engagement with the femoral prosthesis and the femur via the self-locking adjustable flexible member construct in an absence of a knot;
wherein coupling the first portion of the self-locking adjustable flexible member construct to the first attachment region includes coupling a fixed length portion of the self-locking adjustable flexible member construct extending from a pair of passage portions of the self-locking adjustable flexible member construct to a discrete area of the first attachment region of the femoral prosthesis; and
wherein coupling the second portion of the self-locking adjustable flexible member construct to the second attachment region includes coupling a pair of adjustable loops extending from the pair of passage portions to a discrete area of the second attachment region of the femoral prosthesis.

10. A method for trochanteric reattachment, comprising:
positioning a femoral prosthesis relative to a proximal portion of a femur;
coupling a first portion of a self-locking adjustable flexible member construct to a first attachment region of the femoral prosthesis;
coupling a second portion of the self-locking adjustable flexible member construct to a second attachment region of the femoral prosthesis, the second portion being opposite the first portion;
positioning a trochanter relative to the femur and a trochanteric engaging region of the femoral prosthesis;
positioning the self-locking adjustable flexible member construct around an outer surface of the trochanter; and
tensioning free ends of the self-locking adjustable flexible member construct to draw the trochanter into secure engagement with the femoral prosthesis and the femur via the self-locking adjustable flexible member construct in an absence of a knot;
forming a first bore through a portion of the trochanter so as to align with the first attachment region of the femoral prosthesis;
positioning a first portion of a second self-locking adjustable flexible member construct through the first bore and retaining the first portion relative to a discrete attachment member of the first attachment region, wherein the first portion includes a flexible anchor slidably coupled thereto; and
tensioning free ends of the second self-locking adjustable flexible member construct to position a second flexible anchor coupled to a second portion of the second self-locking adjustable flexible member construct relative to an opening of the first bore on the outer surface of the trochanter and draw the trochanter into secure engagement with the femoral prosthesis and femur in an absence of a knot.

11. The method of claim 10, further comprising:
forming a second bore through another portion of the trochanter so as to align with the second attachment region of the femoral prosthesis;
positioning a first portion of a third self-locking adjustable flexible member construct through the second bore and retaining the first portion relative to a discrete attachment member of the second attachment region, wherein the first portion of the third flexible member construct includes a flexible anchor slidably coupled thereto; and
tensioning free ends of the third self-locking adjustable flexible member construct to position a second flexible anchor coupled to a second portion of the third self-locking adjustable flexible member construct relative to an opening of the second bore on the outer surface of the trochanter and draw the trochanter into secure engagement with the femoral prosthesis and femur in an absence of a knot.

12. A method for trochanteric reattachment, comprising:
positioning a femoral prosthesis relative to a proximal portion of a femur;
forming first and second bores spaced apart from each other and through a greater trochanter that has been at least partially separated from the femur;
passing a first portion of a self-locking adjustable flexible member construct through the first bore;
coupling the first portion to a first attachment region of the femoral prosthesis;
passing a second portion of the self-locking flexible member construct through the second bore;
coupling the second portion to a second attachment region of the femoral prosthesis opposite of the first attachment region;
positioning the self-locking adjustable flexible member construct around an outer surface of the greater trochanter; and
tensioning free ends of the self-locking adjustable flexible member construct to draw the greater trochanter into secure engagement with the femoral prosthesis and the femur via the self-locking adjustable flexible member construct in an absence of a knot.

13. The method of claim 12, wherein coupling the first portion to the first attachment region of the femoral prosthesis includes positioning a first flexible anchor slidably coupled to a first adjustable loop of the self-locking adjustable flexible member construct through a first aperture defined by the first attachment region and retaining the first adjustable loop relative to the first aperture via the first flexible anchor; and
wherein coupling the second portion to the second attachment region of the femoral prosthesis includes positioning a second flexible anchor slidably coupled to second adjustable loop of the self-locking adjustable flexible member construct through a second aperture defined by the second attachment region and retaining the second adjustable loop relative to the second aperture via the second flexible anchor.

14. The method of claim 13, wherein tensioning free ends of the self-locking adjustable flexible member construct to draw the greater trochanter into secure engagement with the femoral prosthesis and the femur includes sliding the first and second adjustable loops relative to the respective first and second anchors being retained relative to the respective first and second apertures.

15. The method of claim 13, further comprising coupling the first flexible anchor and the second flexible anchor to both the first and second adjustable loops of the self-locking adjustable flexible member construct.

16. The method of claim 12, wherein coupling the first portion to the first attachment region of the femoral prosthesis includes removably coupling a first adjustable loop of the self-locking adjustable flexible member construct to a first tab extending from the first attachment region; and
wherein coupling the second portion to the second attachment region of the femoral prosthesis includes removably coupling a second adjustable loop of the self-locking adjustable flexible member construct to a second tab extending from the second attachment region.

17. The method of claim 16, wherein the first and second adjustable loops extend from opposite sides of a passage portion of the self-locking adjustable flexible member construct.

18. The method of claim 16, further comprising coupling the first and second adjustable loops to the first tab and the second tab.

19. The method of claim 12, further comprising:
coupling a first adjustable loop of a second self-locking adjustable flexible member construct to the first attachment region of the femoral prosthesis at a location different than the first portion;
coupling a second adjustable loop of the second self-locking adjustable flexible member construct to the second attachment region of the femoral prosthesis at a location different than the second portion;
positioning the second self-locking adjustable flexible member construct around the outer surface of the greater trochanter; and
tensioning free ends of the second self-locking adjustable flexible member construct to draw the greater trochanter into secure engagement with the femoral prosthesis and the femur in an absence of a knot.

20. A method for trochanteric reattachment, comprising:
positioning a femoral prosthesis relative to a proximal portion of a femur, the femoral prosthesis including first and second attachment regions each having a plurality of attachment members spaced apart from each other and arranged at increasing distances from a proximal end of the prosthesis toward a distal end, the first and second attachment regions being on opposite sides of the femoral prosthesis;
coupling a first portion of a first self-locking adjustable flexible member construct to a first attachment member of the first attachment region;
coupling a second portion of the first self-locking adjustable flexible member construct to a second attachment member of the second attachment region;
coupling a first portion of a second self-locking adjustable flexible member construct to a third attachment member of the first attachment region;
coupling a second portion of the second self-locking adjustable flexible member construct to a fourth attachment member of the second attachment region;
positioning the first and second self-locking adjustable flexible member constructs around an outer surface of a greater trochanter such that the first and second self-locking adjustable flexible member constructs overlap each other; and
tensioning free ends of the first and second self-locking adjustable flexible member constructs to draw the greater trochanter into secure engagement with the femoral prosthesis and the femur via the self-locking adjustable flexible member construct in an absence of a knot.

21. The method of claim 20, wherein coupling the first and second portions of the first self-locking adjustable flexible member construct to the respective first and second attachment members includes coupling first and second flexible anchors slidable coupled to adjustable loops of the first self-locking adjustable flexible member construct to the respective first and second attachment members; and
wherein coupling the first and second portions of the second self-locking adjustable flexible member construct to the respective third and fourth attachment members includes coupling third and fourth flexible anchors slidable coupled to adjustable loops of the second self-locking adjustable flexible member construct to the respective third and fourth attachment members.

22. The method of claim 20, wherein positioning the first and second self-locking adjustable flexible member constructs around the outer surface of the greater trochanter includes positioning the first and second self-locking adjustable flexible member constructs around the outer surface of the greater trochanter such that the first and second self-locking adjustable flexible member constructs overlap each other in an X-shaped pattern.

23. The method of claim 20, further comprising:
positioning the first and second portions of the first self-locking adjustable flexible member construct through respective first and second bores formed through the greater trochanter in alignment with the respective first and second attachment members; and
positioning the first and second portions of the second self-locking adjustable flexible member construct through respective third and fourth bores formed through the greater trochanter in alignment with the respective third and fourth attachment members.

24. A method for reattachment of a bone, comprising:
positioning a prosthesis relative to a proximal portion of a first bone;
coupling a first portion of a self-locking adjustable flexible member construct to a first attachment region of the prosthesis;
positioning a second bone portion relative to the first bone proximal portion and a second bone engaging region of the prosthesis;
coupling a second portion of the self-locking adjustable flexible member construct to the second bone portion, the second portion being opposite the first portion;
tensioning free ends of the self-locking adjustable flexible member construct to draw the second bone portion into secure engagement with the prosthesis and the first bone via the self-locking adjustable flexible member construct in an absence of a knot; and
forming a bore through the second bone portion that has been at least partially separated from the first bone; and
wherein coupling the first portion of the self-locking adjustable flexible member construct to the first attachment region of the prosthesis includes coupling the first portion of the self-locking adjustable flexible member construct to a plug member, wherein the plug is coupled to the prosthesis.

25. The method of claim 24, wherein coupling the first portion of the self-locking adjustable flexible member construct to the first attachment region of the prosthesis includes passing the first portion through the bbre formed in the second bone portion and through a through bore in the prosthesis, the plug configured to be at least partially received in the through bore of the prosthesis.

26. The method of claim 25, wherein coupling a second portion of the self-locking adjustable flexible member construct to the second bone portion includes positioning a flexible anchor slidably coupled to the flexible member construct on an outer surface of the second bone portion adjacent the bore; and
wherein tensioning free ends of the self-locking adjustable flexible member construct to draw the second bone portion into secure engagement with the prosthesis and the first bone includes tensioning the free ends to draw the plug into fixed engagement with a side of the through bore opposite a side facing the second bone.

27. The method of claim 24, wherein the first bone includes a femur and the second bone portion includes a greater trochanter of the femur.

28. A method for reattachment of a bone comprising:
positioning a prosthesis relative to a proximal portion of a first bone;
coupling a first portion of a self-locking adjustable flexible member construct to a first attachment region of the prosthesis;
positioning a second bone portion relative to the first bone proximal portion and a second bone engaging region of the prosthesis;
coupling a second portion of the self-locking adjustable flexible member construct to the second bone portion, the second portion being opposite the first portion; and
tensioning free ends of the self-locking adjustable flexible member construct to draw the second bone portion into secure engagement with the prosthesis and the first bone via the self-locking adjustable flexible member construct in an absence of a knot;
wherein the first bone includes a humerus and the second bone portion includes a greater trochanter of the humerus.

* * * * *